(12) United States Patent
Winslow et al.

(10) Patent No.: US 11,826,038 B2
(45) Date of Patent: Nov. 28, 2023

(54) SUTURE ANCHOR CONSTRUCT

(71) Applicant: Biomet Manufacturing, LLC, Warsaw, IN (US)

(72) Inventors: Nathan A. Winslow, Warsaw, IN (US); Hoang Nguyen, Litchfield Park, AZ (US)

(73) Assignee: Biomet Manufacturing, LLC, Warsaw, IN (US)

( * ) Notice: Subject to any disclaimer, the term of this patent is extended or adjusted under 35 U.S.C. 154(b) by 249 days.

(21) Appl. No.: 17/076,401

(22) Filed: Oct. 21, 2020

(65) Prior Publication Data

US 2021/0121168 A1 Apr. 29, 2021

Related U.S. Application Data

(60) Provisional application No. 62/924,868, filed on Oct. 23, 2019, provisional application No. 62/924,802, filed on Oct. 23, 2019.

(51) Int. Cl.
*A61B 17/04* (2006.01)
*A61B 17/16* (2006.01)
*A61F 2/08* (2006.01)

(52) U.S. Cl.
CPC ...... *A61B 17/0401* (2013.01); *A61B 17/0485* (2013.01); *A61B 17/16* (2013.01); *A61B 2017/044* (2013.01); *A61B 2017/0414* (2013.01); *A61B 2017/0427* (2013.01); *A61B 2017/0446* (2013.01); *A61B 2017/0451* (2013.01); *A61B 2017/0458* (2013.01);

(Continued)

(58) Field of Classification Search
CPC .... A61B 2017/0414; A61B 2017/0458; A61B 2017/0446; A61B 2017/0459
See application file for complete search history.

(56) References Cited

U.S. PATENT DOCUMENTS

| 9,107,653 | B2 * | 8/2015 | Sullivan |
| 10,034,663 | B1 | 7/2018 | Nason et al. |
| 10,092,288 | B2 | 10/2018 | Denham et al. |

(Continued)

FOREIGN PATENT DOCUMENTS

| EP | 2429409 A1 | 3/2012 |
| WO | WO-2012088496 A2 | 6/2012 |

OTHER PUBLICATIONS

"European Application Serial No. 20203406.2, Extended European Search Report dated Mar. 17, 2021", 12 pgs.

(Continued)

*Primary Examiner* — Ryan J. Severson
(74) *Attorney, Agent, or Firm* — SCHWEGMAN LUNDBERG & WOESSNER, P.A.

(57) ABSTRACT

Disclosure herein are knotless suture anchor constructs and methods of use thereof. The suture anchor constructs can include a bone anchor and a suture. The bone anchor can include a suture anchoring member and can define a cavity and a longitudinal passage extending from a trailing end of the bone anchor at least partially therethrough to the cavity. The suture anchoring member can be located in the cavity. The suture can be coupled to the suture anchoring member and can include a tensioning portion, a repair portion, and an intermediate portion. The intermediate portion can form a suture loop extending along the longitudinal passage.

19 Claims, 19 Drawing Sheets

(52) U.S. Cl.
CPC .............. *A61B 2017/0459* (2013.01); *A61F 2002/0888* (2013.01)

(56) References Cited

U.S. PATENT DOCUMENTS

| | | |
|---|---|---|
| 10,426,456 B2 * | 10/2019 | Pamichev et al. |
| 2010/0016892 A1 | 1/2010 | Kaiser et al. |
| 2016/0128682 A1 | 5/2016 | Konrath et al. |
| 2017/0049431 A1 | 2/2017 | Dooney, Jr. |
| 2017/0189007 A1 | 7/2017 | Burkhart et al. |

OTHER PUBLICATIONS

"European Application Serial No. 20203406.2, Response filed Oct. 28, 2021 to Extended European Search Report dated Mar. 17, 2021", 13 pgs.

* cited by examiner

SUTURE ANCHOR CONSTRUCT

PRIORITY CLAIM

This application claims the benefit of U.S. Provisional Patent Application Ser. No. 62/924,802, filed on Oct. 23, 2019, and also claims the benefit of U.S. Provisional Patent Application Ser. No. 62/924,868, filed on Oct. 23, 2019, the benefit of priority of each of which is claimed hereby, and each of which are incorporated by reference herein in its entirety.

FIELD OF THE DISCLOSURE

The present subject matter relates to surgical procedures and devices and, more particularly, to prostheses and systems related to soft tissue repair. More specifically, the present disclosure relates to knotless suture anchor constructs and methods of use thereof.

BACKGROUND

The successful reattachment of soft tissue to bone can be a significant concern, especially in the sports medicine industry. The majority of soft tissue repairs involve suture anchors or tacks. In such methods, an anchor or tack is readied for insertion into bone and a suture is passed through tissue and the anchor or tack and knotted or otherwise connected thereto. While holding tension on the suture, joint stability is evaluated and the anchor or tack is deployed into the bone, finalizing the repair.

SUMMARY

To better illustrate the systems and methods disclosed herein, a non-limiting list of examples is provided here:

Example 1 is a suture anchor construct comprising: a bone anchor including a suture anchoring member, the bone anchor defining a cavity and a longitudinal passage extending from a trailing end of the bone anchor at least partially therethrough to the cavity, the suture anchoring member located in the cavity; and a suture coupled to the suture anchoring member and including a tensioning portion, a repair portion, and an intermediate portion, the intermediate portion forming a suture loop extending along the longitudinal passage.

In Example 2, the subject matter of Example 1 optionally includes wherein the tension portion and the repair portion extend from the suture anchoring member through the longitudinal passage.

In Example 3, the subject matter of any one or more of Examples 1-2 optionally include wherein the tension portion or the repair portion extend from the suture anchoring member through the longitudinal passage.

In Example 4, the subject matter of Example undefined optionally includes wherein the repair portion of the suture includes one or more protuberances.

In Example 5, the subject matter of any one or more of Examples 1-4 optionally include wherein a second end of the repair portion is wrapped around the suture anchoring member.

In Example 6, the subject matter of any one or more of Examples 1-5 optionally include wherein a second end of the repair portion passes through the suture anchoring member.

In Example 7, the subject matter of any one or more of Examples 1-6 optionally include a snare passing through a first radial passage and the suture loop, the snare defining a snare loop sized to allow a portion of the repair portion to pass through the snare loop.

In Example 8, the subject matter of any one or more of Examples 1-7 optionally include wherein an exterior surface of the bone anchor forms threads or barbs.

In Example 9, the subject matter of any one or more of Examples 1-8 optionally include wherein the bone anchor is formed of a polyether ether ketone (PEEK) polymer or a biocomposite material.

In Example 10, the subject matter of any one or more of Examples 1-9 optionally include wherein the intermediate portion is a constriction construct that couples the tensioning portion and the repair portion.

In Example 11, the subject matter of any one or more of Examples 1-10 optionally include wherein the repair potion includes a knot configured to prevent the repair portion from being drawn further around the suture anchoring member during or after tensioning of at least one of the tensioning portion and the repair portion.

In Example 12, the subject matter of any one or more of Examples 1-11 optionally include wherein, when implanted, the repair potion is located in between the bone anchor and bone to prevent the repair portion from being drawn further around the suture anchoring member during or after tensioning of at least one of the tensioning portion and the repair portion.

In Example 13, the subject matter of any one or more of Examples 1-12 optionally include wherein the suture anchoring member is tapered proximally having a smaller cross-sectional area at a leading end thereof relative to the trailing end.

In Example 14, the subject matter of any one or more of Examples 1-13 optionally include wherein the suture anchoring member is round.

In Example 15, the subject matter of any one or more of Examples 1-14 optionally include a first radial passage; and a second radial passage, the suture anchoring member located proximate the second radial passage, the first and second radial passages extending through the bone anchor.

In Example 16, the subject matter of Example 15 optionally includes wherein a portion of the repair portion passes through the first or second radial passage.

In Example 17, the subject matter of any one or more of Examples 15-16 optionally include a snare passing through the first radial passage and the suture loop, the snare defining a snare loop sized to allow a portion of the repair portion to pass through the snare loop.

In Example 18, the subject matter of any one or more of Examples 7-17 optionally include wherein the snare and the suture each is a braided material.

Example 19 is a suture anchor construct comprising: a bone anchor including a suture anchoring member, the bone anchor defining: a first radial passage located proximate a trailing end of the bone anchor, a second radial passage locate in between the first radial passage and a leading end of the bone anchor, the suture anchoring member located in the second radial passage, and a longitudinal passage extending from the trailing end of the bone anchor to the second radial passage, the first and second radial passages extending through the bone anchor; a suture including a tensioning portion, a repair portion, and an intermediate portion located in between the tensioning portion and the repair portion, the repair portion extending from the suture anchoring member, the intermediate portion forming a suture loop extending along the longitudinal passage; and a snare passing through the first radial passage and the suture loop.

In Example 20, the subject matter of Example 19 optionally includes wherein the snare defines a snare loop sized to allow a second end of the repair portion to pass through the snare loop.

In Example 21, the subject matter of any one or more of Examples 19-20 optionally include wherein the repair portion of the suture includes one or more knots.

In Example 22, the subject matter of any one or more of Examples 19-21 optionally include wherein the snare and the suture each is a braided material.

In Example 23, the subject matter of any one or more of Examples 19-22 optionally include wherein an exterior surface of the bone anchor forms threads or barbs.

In Example 24, the subject matter of any one or more of Examples 19-23 optionally include wherein the bone anchor is formed of a polyether ether ketone (PEEK) polymer or a biocomposite material.

In Example 25, the subject matter of any one or more of Examples 19-24 optionally include wherein the first end of the repair portion is wrapped around the suture anchoring member.

In Example 26, the subject matter of any one or more of Examples 19-25 optionally include wherein the first end of the repair portion passes through the suture anchoring member.

Example 27 is a method of securing tissue to bone, the method comprising: drilling a hole in the bone; placing a bone anchor into the hole, the bone anchor including a suture extending therefrom, the suture including a repair portion, a tensioning portion, and an intermediate portion forming a suture loop along a longitudinal hole defined by the bone anchor; securing the tissue with the repair portion of the suture; passing a first end of the repair portion of the suture through a radial passage of the bone anchor and the suture loop; and pulling the tensioning portion of the suture to cause the suture loop to pass through the longitudinal hole and contract around the repair portion of the suture.

In Example 28, the subject matter of Example 27 optionally includes wherein securing the tissue to the repair portion of the suture includes passing the repair portion of the suture through the tissue.

In Example 29, the subject matter of any one or more of Examples 27-28 optionally include wherein securing the tissue to the repair portion of the suture includes encircling the tissue with the repair portion of the suture.

In Example 30, the subject matter of any one or more of Examples 27-29 optionally include wherein passing the first end of the repair portion of the suture through the radial passage includes: passing the first end of the repair portion of the suture through a snare loop; and pulling the snare loop through the radial passage.

In Example 31, the subject matter of any one or more of Examples 27-30 optionally include tying a knot in the repair portion of the suture.

In Example 32, the subject matter of Example 31 optionally includes wherein passing the first end of the repair portion of the suture through the radial passage includes passing the knot through the suture loop.

In Example 33, the subject matter of any one or more of Examples 27-32 optionally include tying a knot in the repair portion of the suture after passing the first end of the repair portion of the suture through the radial passage.

In Example 34, the subject matter of any one or more of Examples 27-33 optionally include wherein drilling the hole in the bone include attaching a drill guide to the bone.

In Example 35, the subject matter of Example 34 optionally includes wherein placing the bone anchor into the hole includes passing the bone anchor through the drill guide.

Example 36 is a system for anchoring tissue to a bone, comprising: an anchor having a first body portion and a second body portion, wherein the first body portion has an inner passage extending longitudinally therein and the second body portion has an interior cavity communicating with the inner passage, wherein the second body portion has a suture anchoring member positioned in the inner cavity adjacent of the inner passage, and wherein the interior cavity has a first side opening on a side of the second body portion and has a second side opening another side of the second side portion; a first suture portion wrapping at least a portion of the suture anchoring member and having a locking loop that extends into the inner passage; a second suture portion coupled to the first suture portion around the at least a portion the suture anchoring member and passing through one of the inner passage or the first side opening; and a third suture portion coupled to the second suture portion around the at least the portion of the suture anchoring member and passing through one of the inner passage or the second side opening, wherein the third suture portion couples with the tissue and passes through the locking loop.

In Example 37, the subject matter of Example 36 optionally includes wherein the second suture portion and the third suture portion are coupled by a ziploop.

In Example 38, the subject matter of any one or more of Examples 36-37 optionally include wherein the third suture portion has a knot configured to prevent the third suture portion from being drawn further around the suture anchoring member during or after tensioning of at least one of the second suture portion and the third suture portion.

In Example 39, the subject matter of any one or more of Examples 36-38 optionally include wherein the third suture portion has a plurality of knots there along configured to ratchet against the tissue.

In Example 40, the subject matter of any one or more of Examples 36-39 optionally include a snare configured to pass through the locking loop and configured to pass the third suture portion through the locking loop.

In Example 41, the subject matter of any one or more of Examples 36-40 optionally include wherein the suture anchoring member is tapered proximally having a smaller cross-sectional area at a proximal end thereof relative to a distal end thereof.

In Example 42, the subject matter of any one or more of Examples 36-41 optionally include a second passage in the anchor communicating with the inner passage, and wherein the locking loop extends from an opening of the inner passage or the locking loop is accessible via the second passage.

Example 43 is a system for anchoring tissue to a bone, comprising: an anchor having a longitudinally extending inner passage with a proximal opening and a suture anchoring member positioned in an inner cavity of the anchor distal to the inner passage; a first suture portion wrapping at least a portion of the suture anchoring member and having a locking loop that extends into the inner passage; a second suture portion coupled to the first suture portion around the at least a portion the suture anchoring member and passing through one of the inner passage or a first side opening through a wall in the anchor; and a third suture portion coupled to the second suture portion around the at least the portion of the suture anchoring member and passing through one of the inner passage or a second side opening through the wall in the anchor, wherein the third suture portion couples with the tissue and passes through the locking loop.

In Example 44, the subject matter of Example 43 optionally includes wherein the second suture portion and the third suture portion are coupled by a ziploop.

In Example 45, the subject matter of Example 44 optionally includes wherein the ziploop is part of the first suture portion.

In Example 46, the subject matter of any one or more of Examples 43-45 optionally include wherein the third suture portion has a knot configured to prevent the third suture portion from being drawn further around the suture anchoring member during or after tensioning of at least one of the second suture portion and the third suture portion.

In Example 47, the subject matter of any one or more of Examples 43-46 optionally include wherein the third suture portion has a plurality of knots there along configured to ratchet against the tissue.

In Example 48, the subject matter of any one or more of Examples 43-47 optionally include a snare configured to pass through the locking loop and configured to pass the third suture portion through the locking loop.

In Example 49, the subject matter of any one or more of Examples 43-48 optionally include wherein the suture anchoring member is tapered proximally having a smaller cross-sectional area at a proximal end thereof relative to a distal end thereof.

In Example 50, the subject matter of any one or more of Examples 43-49 optionally include a second passage in the anchor communicating with the inner passage, and wherein the locking loop extends from an opening of the inner passage or the locking loop is accessible via the second passage.

Example 51 is a device for anchoring tissue to a bone, the device comprising: a proximal body portion having an outer surface configured to engage the bone of a patient and defining an inner passage extending longitudinally therealong; an intermediate body portion having an interior cavity communicating with the inner passage, the interior cavity having a first side opening on a first side of the intermediate body portion and having a second side opening on a second side of the intermediate portion, wherein the intermediate body portion has a suture anchoring member positioned in the inner cavity distal of the inner passage and accessible by the first side opening and the second side opening; and a distal body portion distal of the interior cavity and the suture anchoring member.

In Example 52, the subject matter of Example 51 optionally includes wherein the suture anchoring member is tapered proximally having a smaller cross-sectional area at a proximal end thereof relative to a distal end thereof.

In Example 53, the subject matter of any one or more of Examples 51-52 optionally include a second passage in the proximal body portion communicating with the inner passage.

In Example 54, the subject matter of any one or more of Examples 51-53 optionally include wherein the first side opening and the second side opening are directly opposite one another across a longitudinal axis of the device.

In Example 55, the subject matter of any one or more of Examples 51-54 optionally include wherein the inner passage has an opening at a proximal end of the proximal body portion, wherein the opening is configured to allow one or more sutures to pass therethrough including a loop.

In Example 56, the suture anchor constructs or methods of any one of or any combination of Examples 1-55 are optionally configured such that all elements or options recited are available to use or select from.

BRIEF DESCRIPTION OF THE FIGURES

The above-mentioned and other features and advantages of this disclosure, and the manner of attaining them, will become more apparent and the disclosure itself will be better understood by reference to the following description of embodiments taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
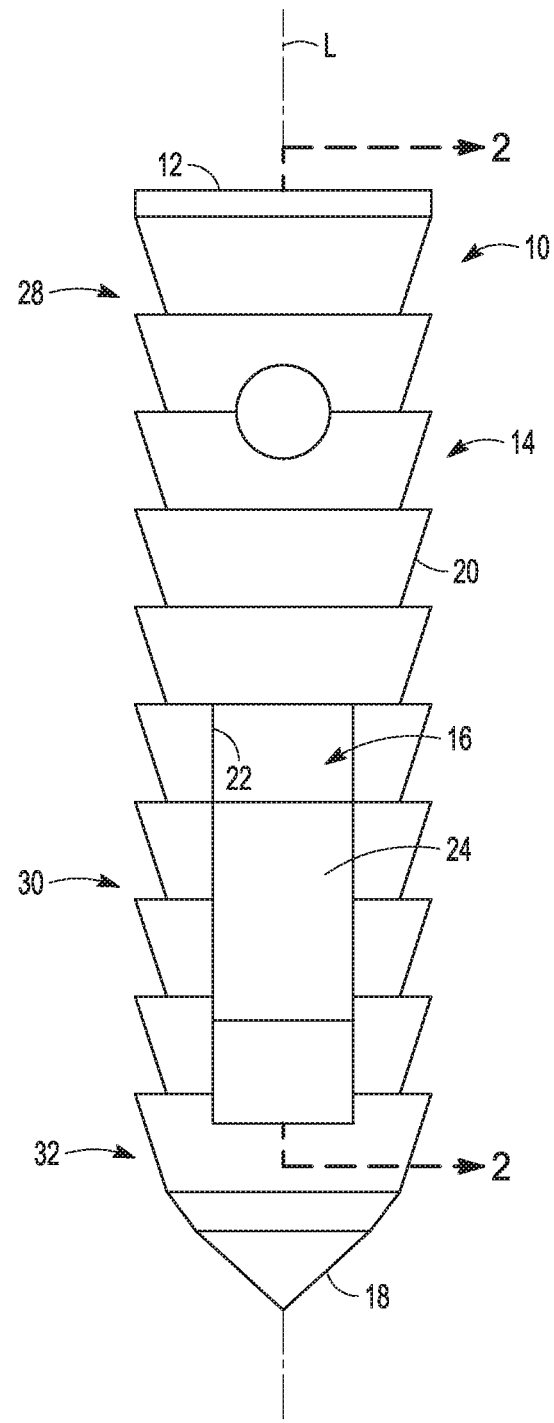
FIG. 1 illustrates an anchoring device in accordance with at least one example of the present disclosure.

Disclosed herein are systems and devices that facilitate the rapid connection of sutures to tissue fixation implants such as a suture anchor. For example, the systems and devices can facilitate the passage of one or more sutures through the suture anchor and the connection of the one or more sutures to the suture anchor. Such connection between the suture anchor and the suture can be accomplished with a minimal change in tension on the one or more sutures connected to the tissue from prior to and after deployment of the suture anchor into bone. Deployment of the suture anchor into bone can be accomplished by a deployment tool, which provides the ability to rapidly and precisely deliver the suture anchor to a desired location, affix the suture anchor to bone and secure the one or more sutures to the suture anchor as will be described herein. In some cases, securement of the one or more sutures to the suture anchor can be down without a deployment tool, such as by hand.

The present inventors have recognized, among other things, that existing soft tissue fixation solutions can require a multiple step process where connection of the suture to the suture anchor can be challenging and time consuming. This process can include deploying an anchor into bone and connecting suture(s) to the deployed anchor. It can often be difficult to accomplish such connection as the suture(s) must be knotted or otherwise connected while maintaining the suture at a desired amount of tension. Failure to provide adequate tension (providing too much or too little) can cause the suture(s) to be ineffective necessitating repetition of the entire process in some cases. Currently known knotless suture anchor constructs typically rely on multiple components that must interact with one another precisely and in a reliable manner to facilitate anchoring of suture.

Considering these and other factors, the present inventors propose an anchoring device and related systems and techniques that can reduce the number of currently used surgical processes to provide for faster, easier, and more reproducible surgical techniques. The anchoring device and related systems can be constructed in a manner so as to maintain suture(s) that are coupled to tissue with a desired amount of tension. Thus, the present application discloses an anchor device and systems where upon deployment of the anchor device, connection of the suture(s) to the anchor is accomplished and a desired tension can be substantially maintained.

The suture anchor constructs and methods disclosed herein can allow a surgeon to fasten tissue to bone without tying a knot. The suture can be at least partially enclosed inside of an anchor inserter until an anchor is deployed in bone. This can allow the surgeon to insert the anchor through a drill guide into the bone, which can then be removed.

After the anchor is inserted into the bone and the drill guide is removed, the surgeon can be left with a suture anchor construct that can include a loop exposed at a top of the anchor and two free strands of suture; a tensioning portion and a repair portion. The repair portion can be passed around and/or through tissue and through the loop. The tensioning portion of the suture can be used to tension the suture anchor construct. As the suture is tensioned by pulling on the tensioning portion, the loop formed by the suture can retract into the anchor, thus pulling part of the repair portion into the anchor with it. As the repair portion gets pulled into the anchor, it can become wedged into the inside of the anchor, thereby locking the repair portion in place and securing the tissue to the bone.

Turning now to the figures, FIG. 1 shows an implantable anchor 10 used in combination with one or more sutures (shown in FIGS. 1-8) for repair of soft tissue. The implantable anchor 10 can be used in combination with a deployment tool (not illustrated) that can be configured for facilitating fixation of the implantable anchor 10 into bone of a patient. The deployment tool can be configured to couple with the implantable anchor 10 at a proximal end 12 (also referred to as a trailing end), for example.

Figure 2:
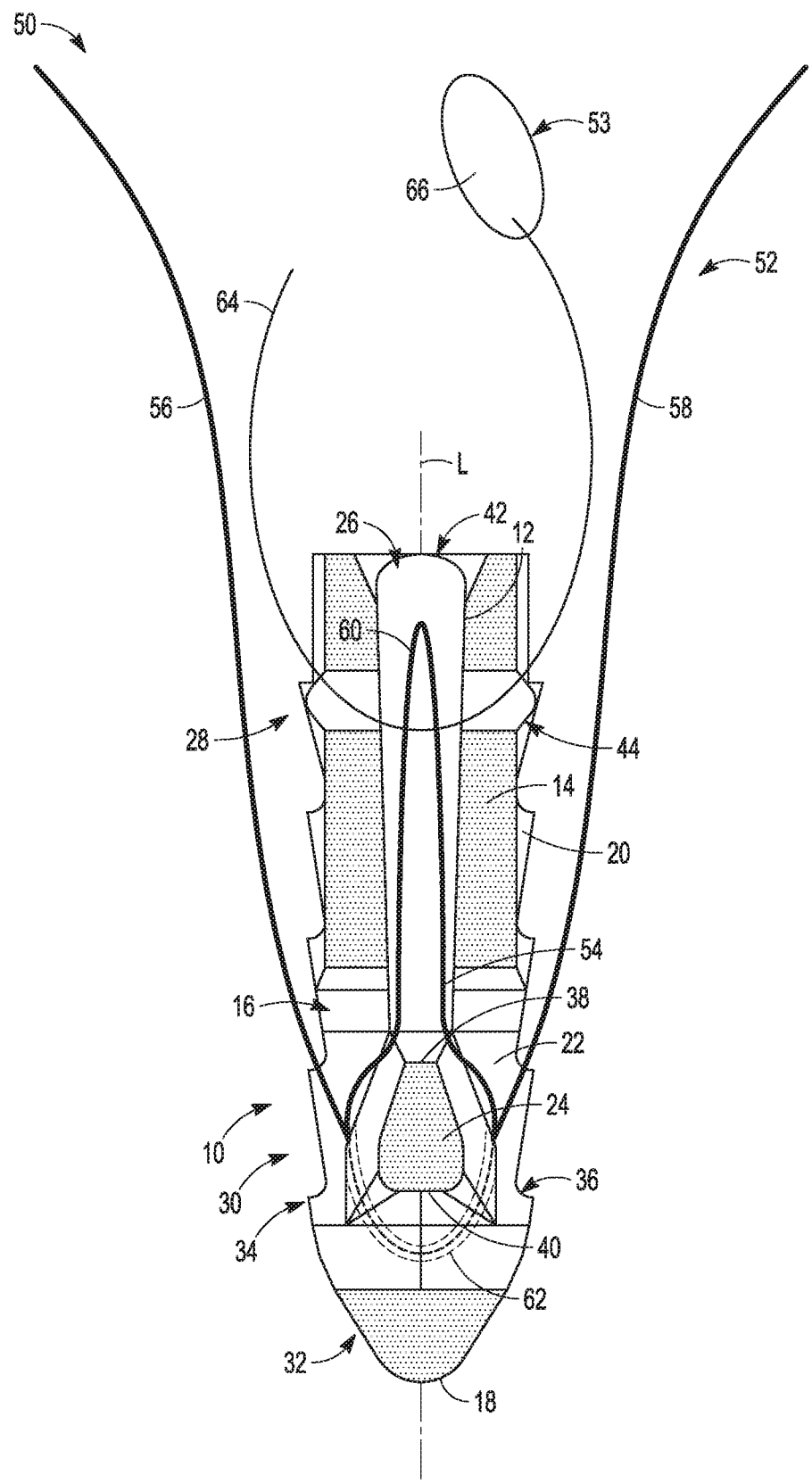
FIG. 2 is a cross-sectional view of the anchoring device of FIG. 1 as part of a first system that includes one or more sutures in accordance with at least one example of the present disclosure.

FIGS. 1 and 2 provide an example of the anchor 10 having a body 14 and an interior cavity 16. The body 14 can have the proximal end 12 and a distal end 18 (also referred to as a leading end) and can be shaped with an exterior surface 20 and an interior surface 22 that defines the interior cavity 16. The body 14 can also include a suture anchoring member 24 and an inner passage 26 (shown in FIG. 2 only).

The anchor 10 and body 14 can include generally a proximal body portion 28 (sometimes referred to as a first body portion herein), an intermediate body portion 30 and a distal body portion 32 arranged along the longitudinal axis L and integrally connected as a single piece. The intermediate body portion 30 and/or the distal body portion 32 are sometimes referred to as a second body portion herein.

In the example of FIGS. 1 and 2, the proximal end portion 28 can include the inner passage 26, for example. The distal body portion 32 can be distal of the interior cavity 16 and the suture anchoring member 24 and can include the distal end 18. The intermediate body portion 30 can include the interior cavity 16 and the suture anchoring member 24. However, in other examples features of the body 14 can be positioned at other portions than those shown. For example, the interior cavity 16 and/or suture anchoring member 24 could be part of the proximal body portion 28 or distal body portion 32 according to other examples. The inner passage 26 could be part of the intermediate body portion and/or the distal body portion 32.

The anchor 10 has an elongate shape along the longitudinal axis L, which extends from the proximal end 12 to the distal end 18. The body 14 can define the interior cavity 16 via the interior surface 22. The body 14 can comprise a wall between the exterior surface 20 and the interior surface 22. The exterior surface 20 can be shaped with features such as grooves, threads, ridges, projections, etc. that facilitate fixation to bone. The exterior surface 20 can be tapered is some examples.

The body 14 can include a first opening 34 and a second opening 36 to the interior cavity 16 and/or the suture anchoring member 24. These openings 34, 36 extend from the longitudinal axis L to the outer surface 20 and extend along the outer surface 20. The openings 34, 36 can be in any of the proximal end portion 28, the intermediate portion 30, and/or the distal portion 32 as desired. The first opening 34 can be in the exterior surface 20 on a first side of the body 14 and the second opening 36 can be in the exterior surface 20 on a second side of the body 14 opposing the first opening 34, for example. However, other relative positions are contemplated. The first opening 34 and the second opening 36 are optional features and need not be used in all examples. The openings 34, 36 facilitate access for the one or more sutures to the interior cavity 16 and the suture anchoring member 24.

The interior cavity 16 can be within any of the proximal end portion 28, the intermediate portion 30, and/or the distal portion 32 as desired. In the example of FIGS. 1 and 2, the interior cavity 16 can be positioned adjacent and in communication with the inner passage 26 (FIG. 2). The interior cavity 16 can be sized and shaped to house the suture anchoring member 24 and the one or more sutures.

Referring now to FIG. 2, the suture anchoring member 24 can be positioned in the interior cavity 16 adjacent (such as distal of) the inner passage 26. The suture anchoring member 24 can comprise a post or bar or similar feature and can be positioned transverse to the longitudinal axis L. Put another way, the suture anchoring member 24 can be configured to be wrapped by or otherwise coupled to the one or more sutures. The suture anchoring member 24 can be tapered proximally to distally having a relatively smaller cross-sectional area at a proximal end 38 relative to a distal end 40.

As shown in FIG. 2, the inner passage 26 can extend generally along the longitudinal axis L from the proximal end 12 to the interior cavity 16. The inner passage 26 can communicate with the interior cavity 16 and can be spaced from the suture anchoring member 24. The inner passage 26 can have a proximal opening 42 at the proximal end 12. However, the proximal opening 42 can be optional to the anchor 10, and therefore, may not be utilized in all embodiments.

As shown in FIG. 2 (and indeed FIG. 1) the anchor 10 can include a second passage 44 spaced from the interior cavity 16 and the proximal end 12. This second passage 44 can pass through the anchor 10 from the first side to the second side (same or different sides as the openings 34, 36) and can extend transverse to the longitudinal axis L. The second passage 44 can intersect with so as to communicate with the inner passage 26. The second passage 44 the proximal opening 42 can be optional to the anchor 10, and therefore, may not be utilized in all embodiments.

FIGS. 2, 3 and 4 also show a system 50 that includes the anchor 10, the one or more sutures 52 and a snare 53 (shown in FIG. 2 only).

The one or more sutures 52 can comprise a plurality of sutures or a single suture. The plurality of sutures if utilized can be coupled together by various methods known in the art so as to comprise an assembly. As subsequently described, this application refers to portions of the one or more sutures 52. It should be recognized these portions can comprise part of one suture, can be formed by separate sutures, or can be formed by a plurality of sutures coupled or otherwise used together.

It should also be noted that the one or more sutures 52 as arranged in the system 50 (or in subsequent systems of others of the figures) can be pre-assembled as shown in FIG. 2, so as to be coupled with the anchor 10 prior to implantation of the anchor 10 into bone of the patient. Thus, the one or more sutures 52 do not need to be further assembled to be coupled with the anchor 10 (or with one another) in vivo other than using the techniques described subsequently in reference to FIGS. 3 and 4. Put another way, the one or more suture 52 can be assembled so as to wrap or otherwise couple with the suture anchoring member 24 prior to implantation of the anchor 10 into bone of the patient. Other features of the one or more sutures 52 that will be described subsequently such as a locking loop, a constriction construct, a tensioning suture and/or a repair suture can also be provided prior to implantation of the anchor 10 into bone of the patient. This pre-assembly eliminates steps for the physician in the surgical process. Thus, the present system 50 simplifies the surgical process and provides for time savings.

The one or more sutures 52 can include a first suture portion 54, a second suture portion 56 and a third suture portion 58. The first suture portion 54 can be referred to as an intermediate portion, the second suture portion 56 can be referred to as a tensioning portion, and the third suture portion 58 can be referred to as a repair portion.

The one or more sutures 52 can be of biocompatible material(s) for example polymer or a knit or woven textile such as a braided nylon material. The first suture portion 54 can wrap or otherwise couple with at least a portion of the suture anchoring member 24. The first suture portion 54 can additionally along another portion of the extent thereof have a locking loop 60 (sometimes referred to as a snare loop) that is configured to and extends into the inner passage 26. The locking loop 60 can extend proximally from the suture anchoring member 24 and can be disposed generally on an opposing side of the suture anchoring member 24 from a part of the first suture portion 54 that wraps the distal portion of the suture anchoring member 24.

A part of first suture portion 54 such as the part that wraps the distal portion of the suture anchoring member 24 can be configured as a constriction construct 62 in some examples. However, in other examples the constriction construct 62 can comprise a separate component of the system 50 and not a feature of the first suture portion 54. In yet other examples, the constriction construct 62 can be part of the second suture portion 56 or the third suture portion 58. Constriction construct 62 can also be several constriction constructs each configured to receive a different one of the suture portions discussed or configured to receive different portions of the length of one or more of the suture portions discussed, for example. For simplicity, the description below assumes the constriction construct 62 is part of the first suture portion 54 and only a single constriction construct is shown and discussed. It should be recognized however that other configurations are contemplated.

Figure 3A:
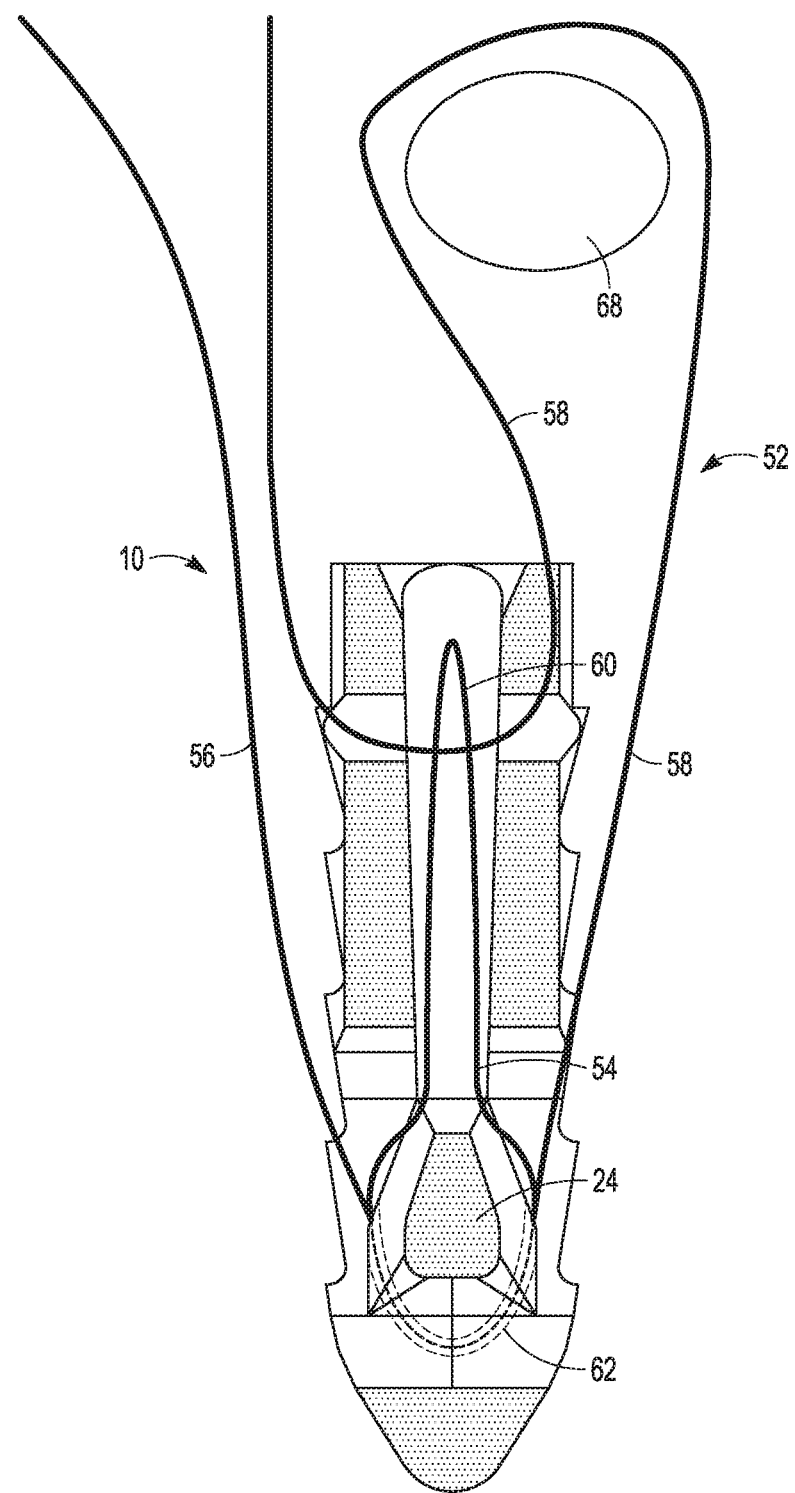
FIG. 3A shows the first system of FIG. 2 initially capturing tissue and coupling back to the anchoring device in accordance with at least one example of the present disclosure.
Figure 3B:
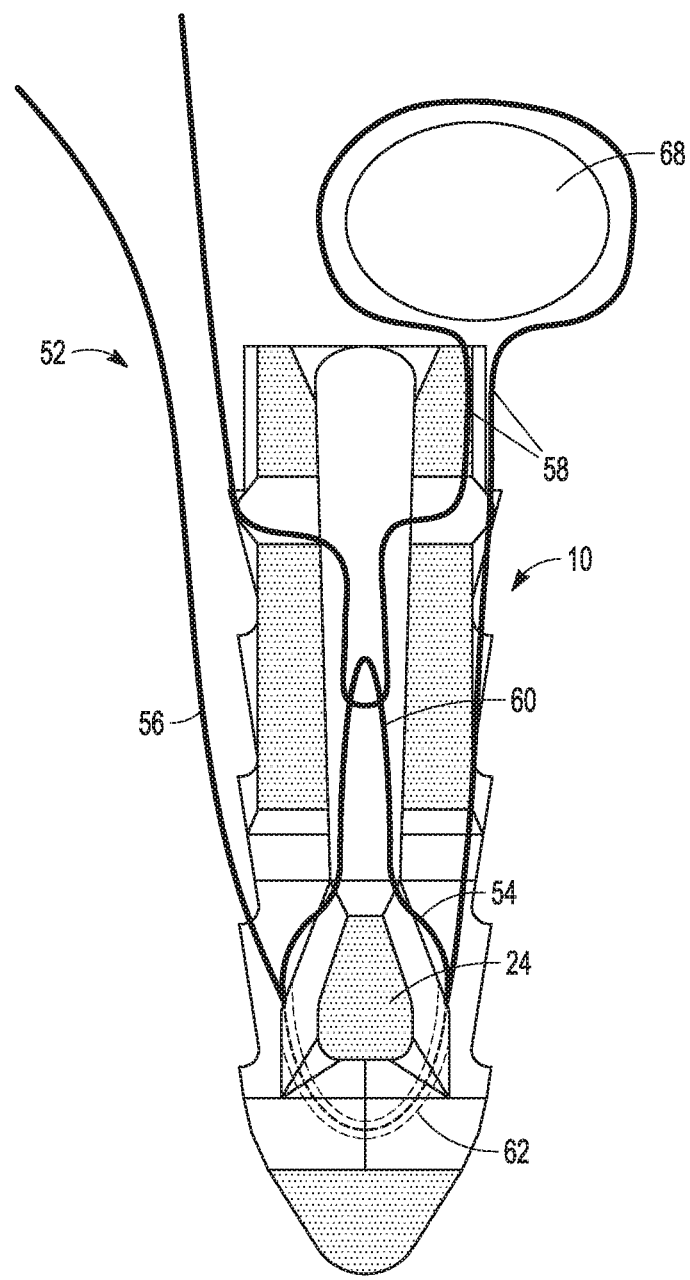
FIG. 3B shows the first system of FIG. 2 further deployed capturing tissue and anchoring back to the anchoring device in accordance with at least one example of the present disclosure.

The constriction construct 62 can comprise a braided body that defines a longitudinally formed hollow passage therein. First and second apertures can be defined in the braided body at first and second end locations of the longitudinally formed passage. Briefly, longitudinal, overlapping and/or parallel placement of the second and/or third suture portions 56 and 58 within the longitudinal passage of the constriction construct 62 resists reverse relative movement of the second and third suture portions 56 and 58 once one or more of the second and third suture portions 56 and 58 are tightened as illustrated in FIGS. 3A and 3B. The first and second apertures can be formed during a braiding process as loose portions between pairs of fibers defining the first suture portion 54. The second and third suture portions 56 and 58 can be passed through the longitudinal passage of the constriction construct 62 a single time or multiple times. It is envisioned that either a single or multiple apertures can be formed at the ends of the longitudinally formed passage of the constriction construct 62 or along a length in between. Upon applying tension to the second suture portion 56 and/or the third suture portion 58, the size of the loop(s) 60 is reduced to a desired size or load. At this point, additional tension causes the body of the constriction construct 62 defining the longitudinal passage to constrict about the second and third suture portions 56 and 58 within the longitudinal passage. This constriction reduces the diameter of the longitudinal passage of the constriction construct 62, thus forming a mechanical interface between the exterior surfaces of the second and third suture portions 56 and 58 as well as the interior surface of the longitudinal passage. This interface restricts loosening movement of the second and third suture portions 56 and 58 such that the constriction construct 62 couples the second and third suture portions 56 and 58 against loosening movement and the constriction construct 62 is maintained against the suture anchoring member 24 by the tension on the locking loop 60.

Thus, according to one example, the constriction construct 62 can be formed of a braided hollow core suture having an exterior surface, wherein said braiding imparts a first coefficient of friction to a first portion of the exterior surface of the braided hollow core suture and a second coefficient of friction to a second portion of the exterior surface of the braided hollow core suture, the first coefficient of friction provided by a first type of fiber that is formed with a first biocompatible material, and the second coefficient of friction provided by a second type of fiber that is formed with a second biocompatible material. For example, the braided structure can include a cylindrical and/or helical wound braid that can form a biaxial braid. As a result, the back tension created by the tension in second and third suture portions 56 and 58 can cause the braids to narrow. The narrowing of the braids causes the braids to grip any portion of third suture portion 58, or the suture in general, that passes through the core of the suture and exits the core between the braids. The more back tension created in second suture portion 56 the tighter the gripping force. Further details regarding the construction of an exemplary constriction construct can be found in U.S. Pat. No. 10,092,288 B2, entitled "Method And Apparatus For Coupling Soft Tissue To A Bone", the entire contents of which are incorporated by reference. An example of a constriction construct includes a ZIPLOOP® manufactured by ZIMMER BIOMET® of Warsaw, Ind.

While the constriction construct 62 can allow for tissue to be secured without the need for knot to be tied, embodiments disclosed herein contemplate that the surgeon can still tie a knot in the second suture portion 56, the third suture portion 58, or both, if desired. For example, once the tissue has been positioned the second and third suture portions 56 and 58 can be tied together, to other bone anchors, to other sutures, etc. to help maintain the tension on the tissue.

Referring now to FIG. 2, the snare 53 can include a flexible portion 64 constructed of a flexible material such as fiber. The snare 53 can comprise a separate instrument also having a threader 66, an eye or eyelet, connected to the flexible portion 64. The threader 66 as well as the flexible portion 64 can be configured for insertion into the anchor 10 such as via the second passage 44 as illustrated in FIG. 2. In particular, the flexible portion 64 can initially be inserted through the second passage 44 and through the locking loop 60. As shown in FIGS. 3A and 3B, the third suture portion 58 can be wrapped or otherwise coupled to the flexible portion 64 or threader 66. The threader 66 with the third suture portion 58 coupled thereto can then be drawn through the second passage 44 via the flexible portion 64 protruding from the anchor 10. Passage of the threader 66 and third suture portion 58 through the locking loop 60 (locking loop 60 acts as an eyelet) results in the third suture portion 58 being coupled to the locking loop 60 (part of the first suture portion 54) as illustrated in FIGS. 3A and 3B. Thus, according to a method shown in FIGS. 2-3B, the anchor 10 can be inserted into bone through a drill guide, which can be a curved or straight drill guide, or other tool. Prior to insertion, as discussed previously, the one or more sutures 52 can be pre-assembled including having the constriction construct 62 and locking loop 60 or another feature facilitating coupling already positioned within the anchor 10. The method can pass the repair suture (the third suture portion 58) through/around etc. tissue 68. The repair suture (the third suture portion 58) can then be passed through the locking loop 60. This can be done by hand or a device such as the snare 53. Importantly, and as shown in other examples herein, the repair suture (the third suture portion 58) need not be passed through the anchor 10 to couple with the locking loop 60. Rather, in some cases the locking loop 60 can protrude from the anchor 10 such as through the proximal opening 42, an opening in the side of the anchor 10 such as the first side opening 34, the second side opening 36, an opening to the second passage 44 or another opening not specifically shown.

Figure 4A:
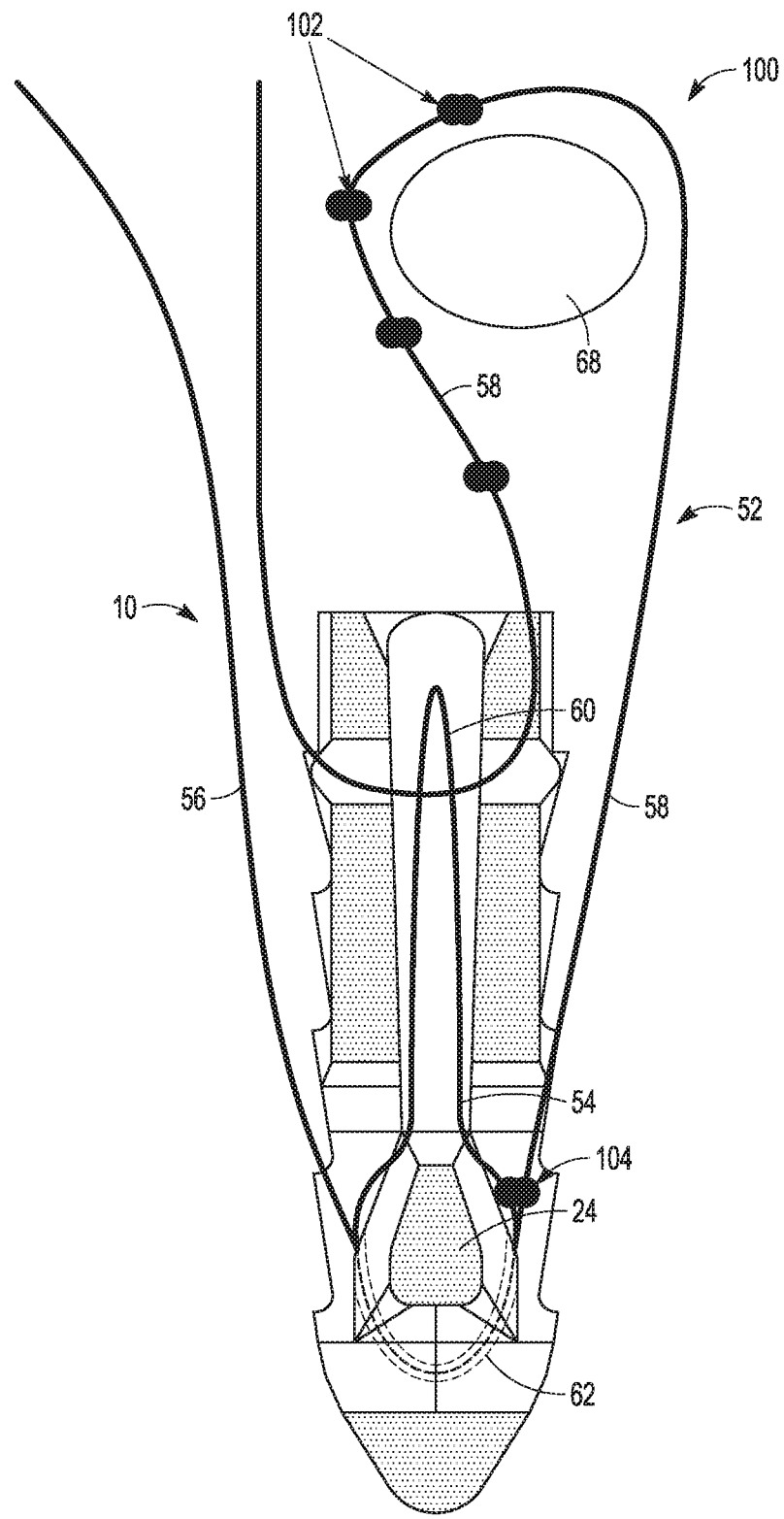
FIG. 4A is a cross-sectional view of a second system that includes the anchoring device of FIG. 1 and one or more sutures initially capturing tissue and coupling back to the anchoring device in accordance with at least one example of the present disclosure.
Figure 4B:
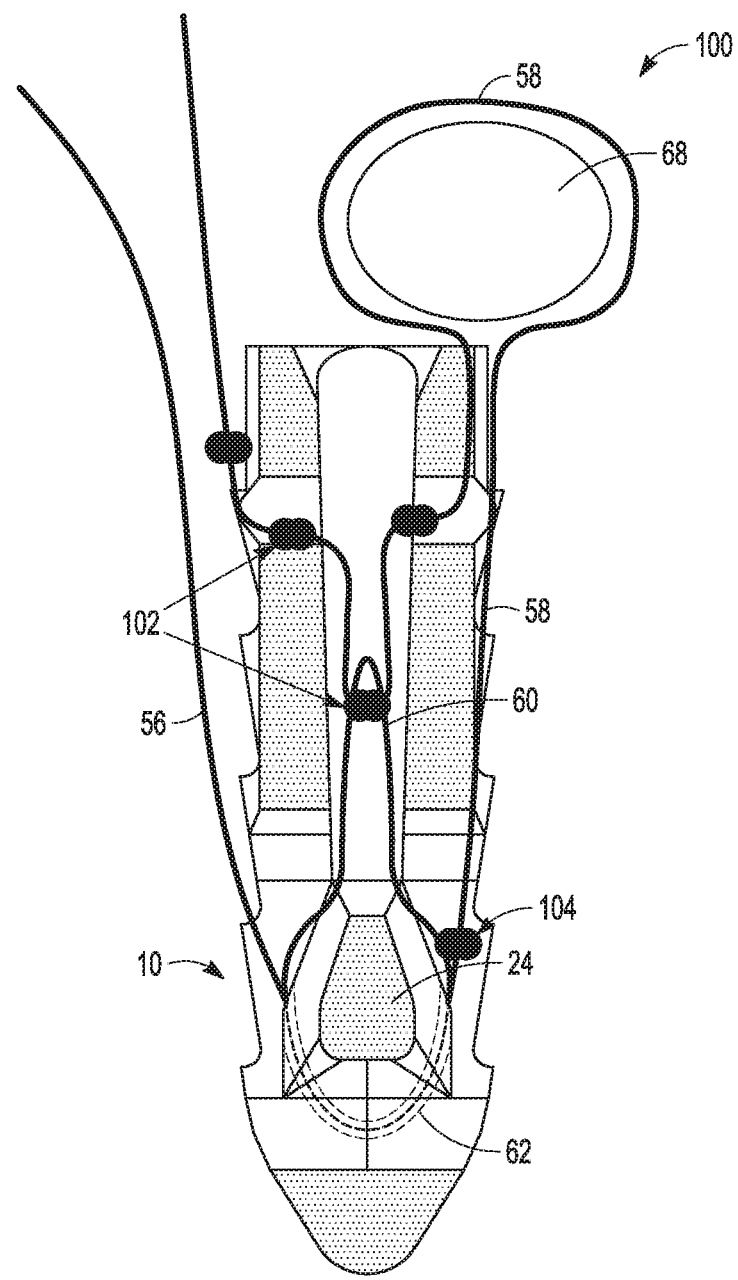
FIG. 4B shows the second system further deployed capturing tissue and anchoring back to the anchoring device in accordance with at least one example of the present disclosure.

FIGS. 4A and 4B show a second system 100 of similar construction to the system 50 previously described. The system 100 includes the anchor 10 as previously described. The second system 100 includes first suture portion 54, the second suture portion 56, the third suture portion 58, the locking loop 60 and the constriction construct 62 as previously described. However, the construct of the repair suture (the third suture portion 58) has been altered from that of the example of FIGS. 2-3B. For example, the third suture portion 58 includes a plurality of knots 102 therealong. Each of the plurality of knots 102 is spaced from others. Such spacing can be a predefined distance according to some examples. The plurality of knots 102 can facilitate coupling to the tissue 68 such as by creating a ratcheting action over and through the tissue 68 as shown in FIG. 4A. Furthermore, as shown in FIG. 4B the plurality of knots 102 can facilitate coupling with the locking loop 60 again by creating a ratcheting action that keeps the third suture portion 58 from easily being slackened and passed back through the locking loop 60.

FIGS. 4A and 4B also show a knot 104 of the third suture portion 58 located at or closely adjacent the constriction construct 62 such as within or closely adjacent the inner cavity 16. This knot 104 is configured to keep the third suture portion 58 (repair suture) from slackening and going backwards during tensioning of the third suture portion 58 and/or the second suture portion 56 as shown in FIGS. 4A and 4B. Thus, the knot 104 of the third suture portion 58 is configured to prevent the third suture portion 58 from being drawn further around the suture anchoring member 24 during or after tensioning of at least one of the second suture portion 56 and the third suture portion 58.

Figure 4C:
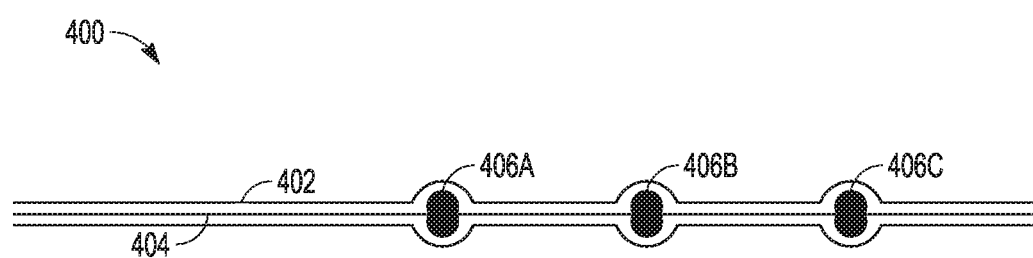
FIG. 4C shows a suture in accordance with at least one example of the present disclosure.

FIG. 4C shows a suture 400 in accordance with at least one example of the present disclosure. The suture 400 can include an inner filament 402 and a sheathing 404. The inner filament 402 can be a monofilament or a braided structure similar to other sutures disclosed herein. The inner filament 402 can be tied into one or more knots 406 (individually, first knot 406A, second knot 406B, third knot 406C, etc.). While FIG. 4C shows only three knots 406, inner filament 402 can be tied into any number of knots 406.

The sheathing 404 can be a braided suture as disclosed herein that encases the inner filament 402. The sheathing can allow for smooth transition to the knots 406 so that when the suture 400 is not under tension, the repair portion or tensioning portion of the suture 400 (or a different suture) can transition the knots 406 without snagging. While under tension, the repair portion or the tensioning portion can compress the sheathing 404 so as to hinder the repair portion or the tensioning form easily slipping over knots 406.

While FIG. 4C shows knots 406, other protuberances can be used in place of knots to create a roughened suture. For example, beads can be secured to inner filament 402. Other structures besides knots and beads can be used to create a bulge around inner filament 402, which can translate into a bulge or otherwise bumpy and/or roughened surface of sheathing 404. For instance, suture 400 can be braided to create a roughened surface. For example, one of the threads within braid can be replaced with a thread having a larger diameter than the other threads within the braid. The larger diameter can cause a roughened surface.

Figure 5:
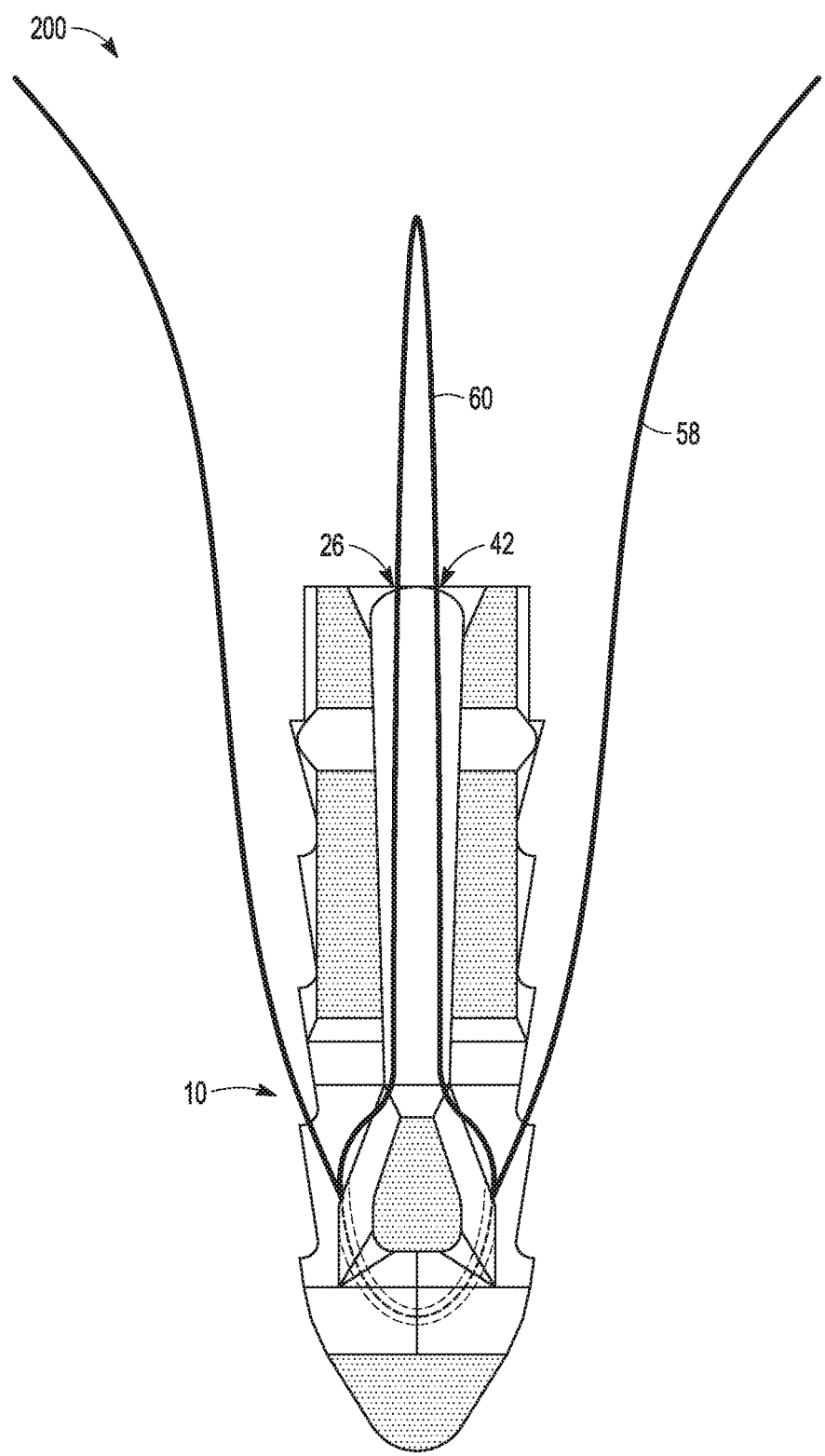
FIG. 5 is a cross-sectional view of the anchoring device of FIG. 1 as part of a third system that includes one or more sutures in accordance with at least one example of the present disclosure.

FIG. 5 shows a third system 200 of similar construction to the system 50 previously described. The system 200 includes the anchor 10 as previously described. However, the system 200 differs in that as illustrated in FIG. 5, the locking loop 60 can be configured to extend from the proximal opening 42 and inner passage 26 to outside of the anchor 10. This can facilitate ease of coupling the third suture portion 58 with the locking loop 60 as the snare 53 (FIG. 2) need not be utilized.

Figure 6:
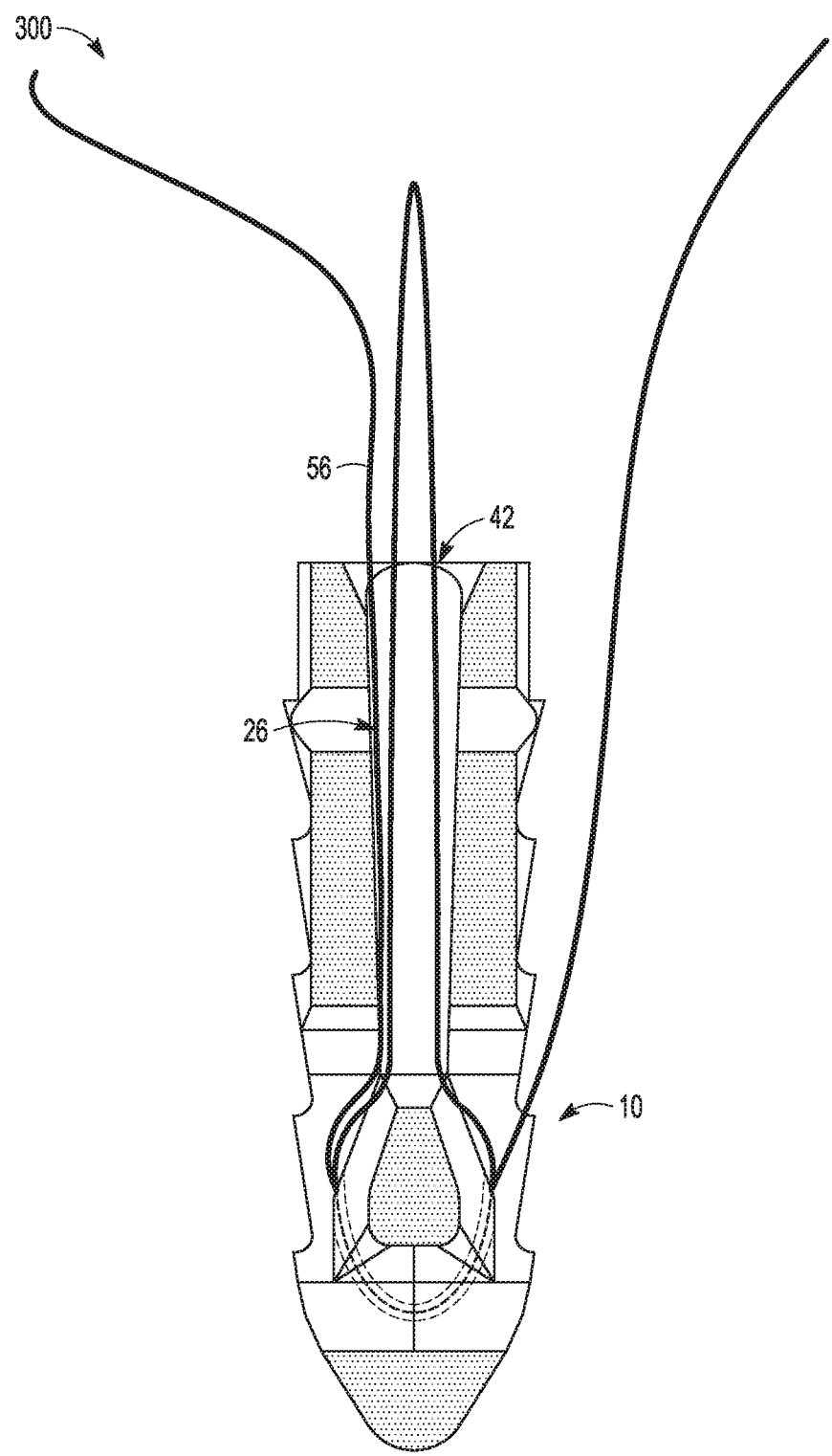
FIG. 6 is a cross-sectional view of the anchoring device of FIG. 1 as part of a fourth system that includes one or more sutures in accordance with at least one example of the present disclosure.

FIG. 6 shows a fourth example system 300 of similar construction to the system 50 previously described including the anchor 10. The system 300 differs in that the second suture portion 56 can extend through the inner passage 26 and pass through the proximal opening 42 rather than extending through one of the side openings as previously illustrated in FIGS. 2-3B.

Figure 7:
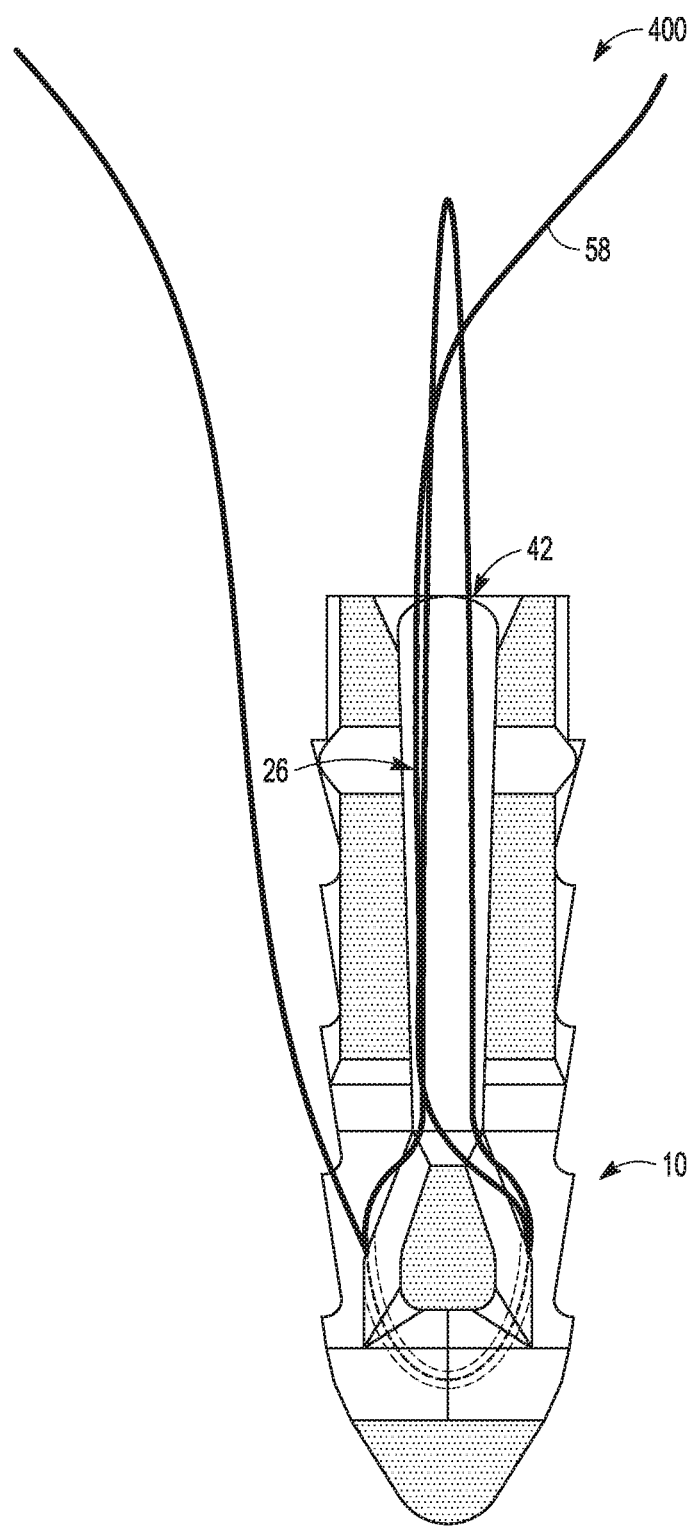
FIG. 7 is a cross-sectional view of the anchoring device of FIG. 1 as part of a fifth system that includes one or more sutures in accordance with at least one example of the present disclosure.

FIG. 7 shows as fifth example system 400 of similar construction to the system 50 previously described including the anchor 10. The system 400 differs in that the third suture portion 58 can extend through the inner passage 26 and pass through the proximal opening 42 rather than extending through one of the side openings as previously illustrated in FIGS. 2-3B.

Figure 8:
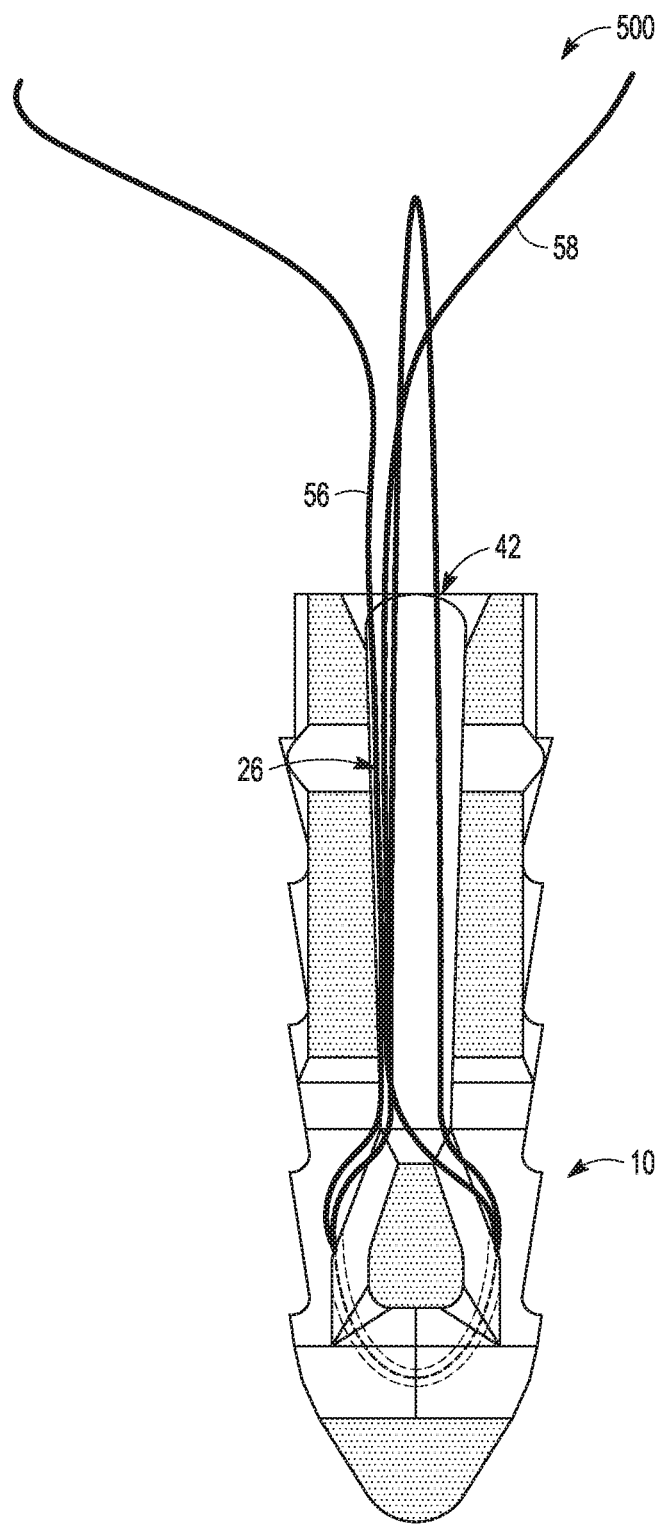
FIG. 8 is a cross-sectional view of the anchoring device of FIG. 1 as part of a sixth system that includes one or more sutures in accordance with at least one example of the present disclosure.

FIG. 8 shows as sixth example system 500 of similar construction to the system 50 previously described including the anchor 10. The system 500 differs in that both the second suture portion 56 and the third suture portion 58 can extend through the inner passage 26 and pass through the proximal opening 42 rather than extending through respective ones of the side openings as previously illustrated in FIGS. 2-3B.

Figure 9:
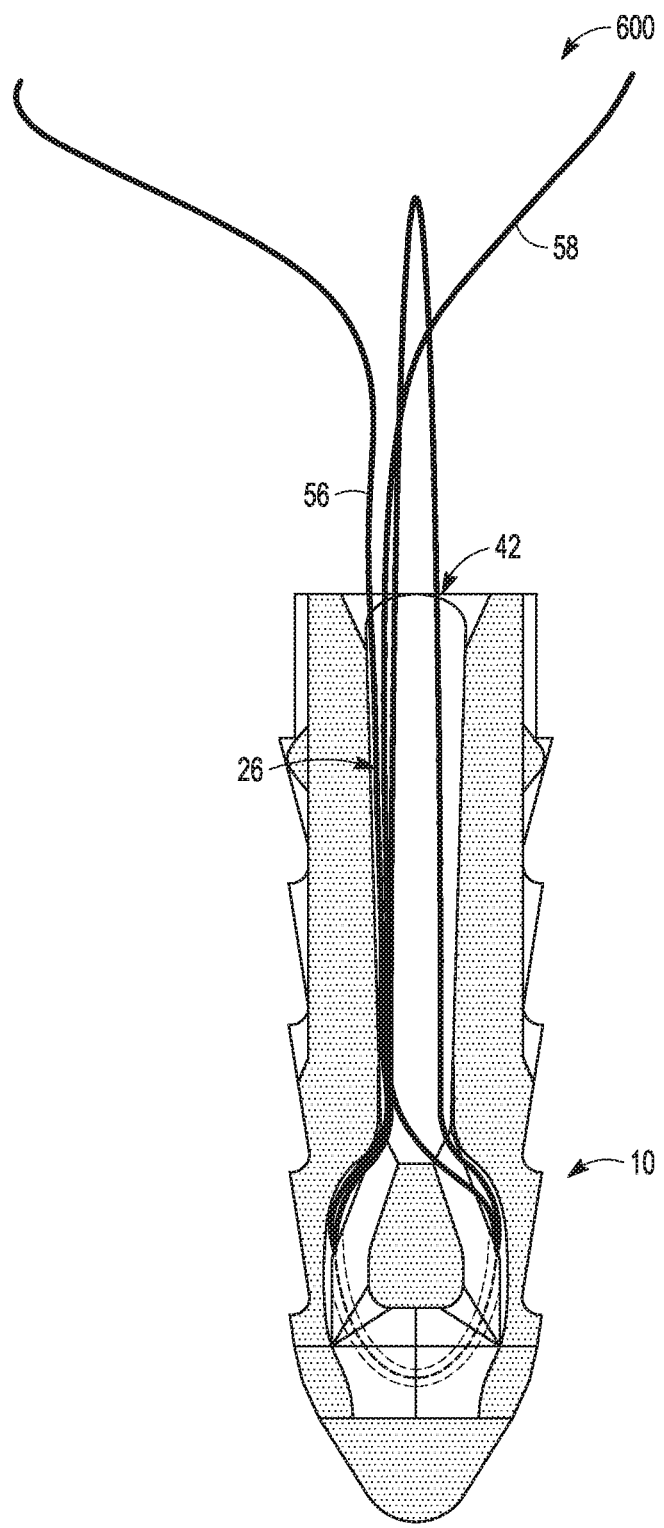
FIG. 9 is a cross-sectional view of the anchoring device of FIG. 1 as part of a seventh system that includes one or more sutures in accordance with at least one example of the present disclosure.

FIG. 9 shows as sixth example system 600 of similar construction to the system 50 previously described including the anchor 10. The system 600 differs the anchor 10 does not include passage 44 and corresponding first opening 34 and the second opening 36 as previously illustrated in FIGS. 2-8. Instead, the first suture portion 54, the second suture portion 56, and the third suture portion 58 can extend through the inner passage 26 and pass through the proximal opening 42. The snare 53 can also pass into and out of the inner passage 26. For example, the middle portion of the flexible portion 64 can pass through the locking loop 60 and both the flexible portion 64 and the threader 66 can project from the proximal opening 42. The third suture portion 58 can be passed through the threader 66 and then pulled through the locking loop 60 as disclosed herein.

Figure 10:
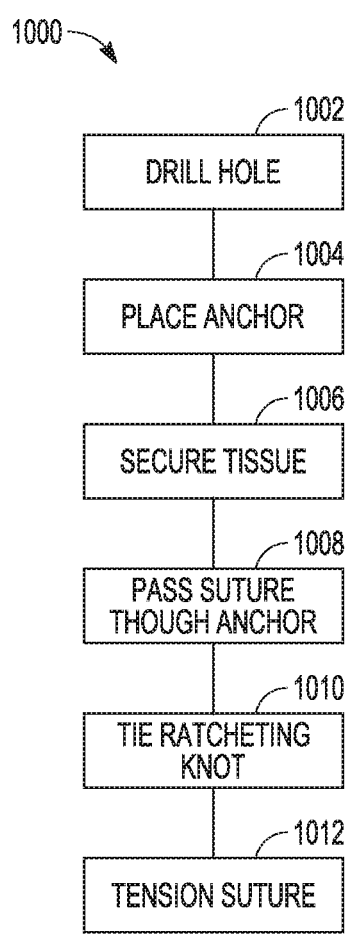
FIG. 10 shows a flowchart for a surgical method in accordance with at least one example of the present disclosure.

FIG. 10 shows a flowchart for a surgical method 1000 in accordance with at least one example of the present disclosure. Surgical method 1000 can be utilized in any surgical procedure that can utilize suture anchor constructs, such as the suture anchor constructs shown and described with respect to FIGS. 2-8 herein. Surgical method 1000 can include drilling a hole in bone (1002). Drilling the hole in the bone can include using guiding instruments. For example, a drill guide can be attached to the bone or other anatomical structure prior to drilling the hole. The drill guide can include a cannulated structure in which a drill bit can pass through.

Once the hole has been drilled in the bone, a bone anchor can be placed into the hole (1004). The bone anchor can be part of a suture anchor construct, such as the suture anchor constructs disclosed herein, and can include one or more sutures that extend from the bone anchor as disclosed herein. The drill guide used to drill the hole in the bone can also be used to place the bone anchor. For example, the bone anchor can be passed through a canula formed by the drill guide and screwed or pressed into the bone thereby securing the bone anchor to the bone. Use of the drill guide can prevent the drilled hole from filling with blood, tissue, or bone fragments. In addition, the drill guide can keep tissue retracted so as not to cover the hole and hinder placement of the bone anchor. Add stuff about trajectory of bone anchor.

Once the bone anchor has been secured to bone, tissue can be secured to a repair portion of the suture (1006). For example, the tissue can be secured to the repair portion of the suture by passing the repair portion of the suture through the tissue. In addition to or in combination with passing the repair portion of the suture through the tissue, the repair portion of the suture can be wrapped around or otherwise encircle the tissue.

After securing the tissue to the suture, a portion of the repair portion of the suture can be passed through the bone anchor (1008). For example, as disclosed herein, a portion of the repair portion of the suture can be passed through a radial passage of the bone anchor and through a suture loop formed by an intermediate portion of the suture. Consistent with embodiments disclosed herein, a snare can be used to pass the portion of the repair portion through the bone anchor. For instance, a portion of the repair portion can be passed through a snare loop formed by the snare. Once part of the suture passes through the snare loop, the snare loop can be pulled through the radial passage of the bone anchor. For example, a free end of the snare can be pulled by the surgeon to pull the snare loop through the bone anchor.

With the repair portion of the suture passing through the bone anchor, a knot can be tied in the repair portion of the suture (1010). The knot can also be tied before the repair portion of the suture is passed through the bone anchor and suture loop in stage 1008. As disclosed herein, one or more knots can be tied. The knots can provide additional friction or other contact surfaces for the suture loop to grip when securing the tissue to the bone.

A tensioning portion of the suture can be pulled (1012). Pulling the tensioning portion of the suture can cause the suture loop to contact the repair portion of the suture and/or a knot. The tension in the suture can cause the tissue to be pulled against the bone or other anatomical structure proximate the bone anchor. The tension in the suture can be maintained by a constriction construct as disclosed herein. In addition to or in combination with the constriction construct structure, the surgeon can tie one or more knots in the tensioning portion, the repair portion, or both portions of the suture to secure the suture and tissue in place.

The various stages of surgical method 1000 have been described in a particular order for ease of discussion and completeness. However, the various stages of surgical method 1000 can be rearranged and/or omitted without departing from the scope of the present disclosure. For example, the tying of knots as described with respect to stage 1010 need not be completed. The suture anchor constructs and surgical methods disclosed herein can be utilized with or without knots without departing from the scope of the present disclosure.

Figure 11A:
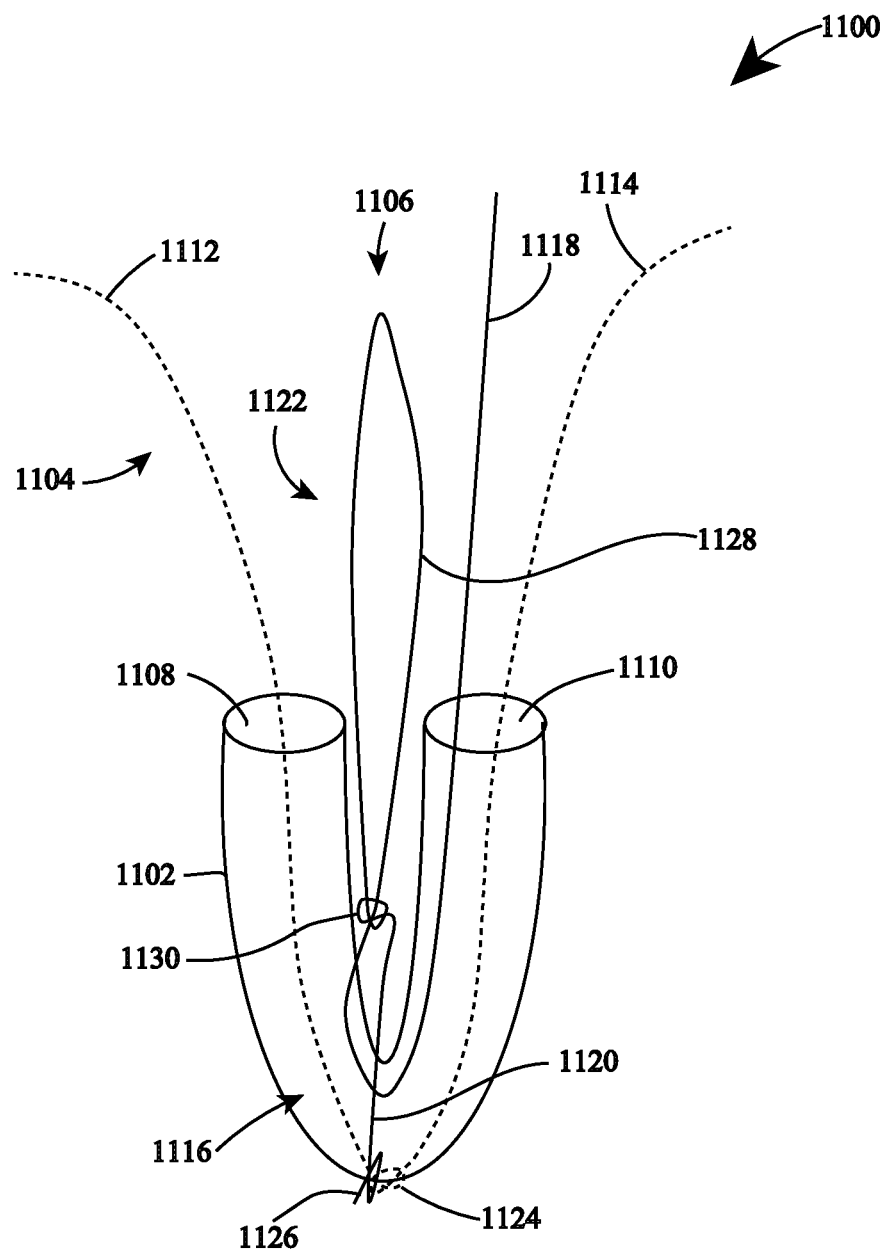
FIGS. 11A, 11B, and 11C show a suture anchor construct in accordance with at least one example of the present disclosure.
Figure 11B:
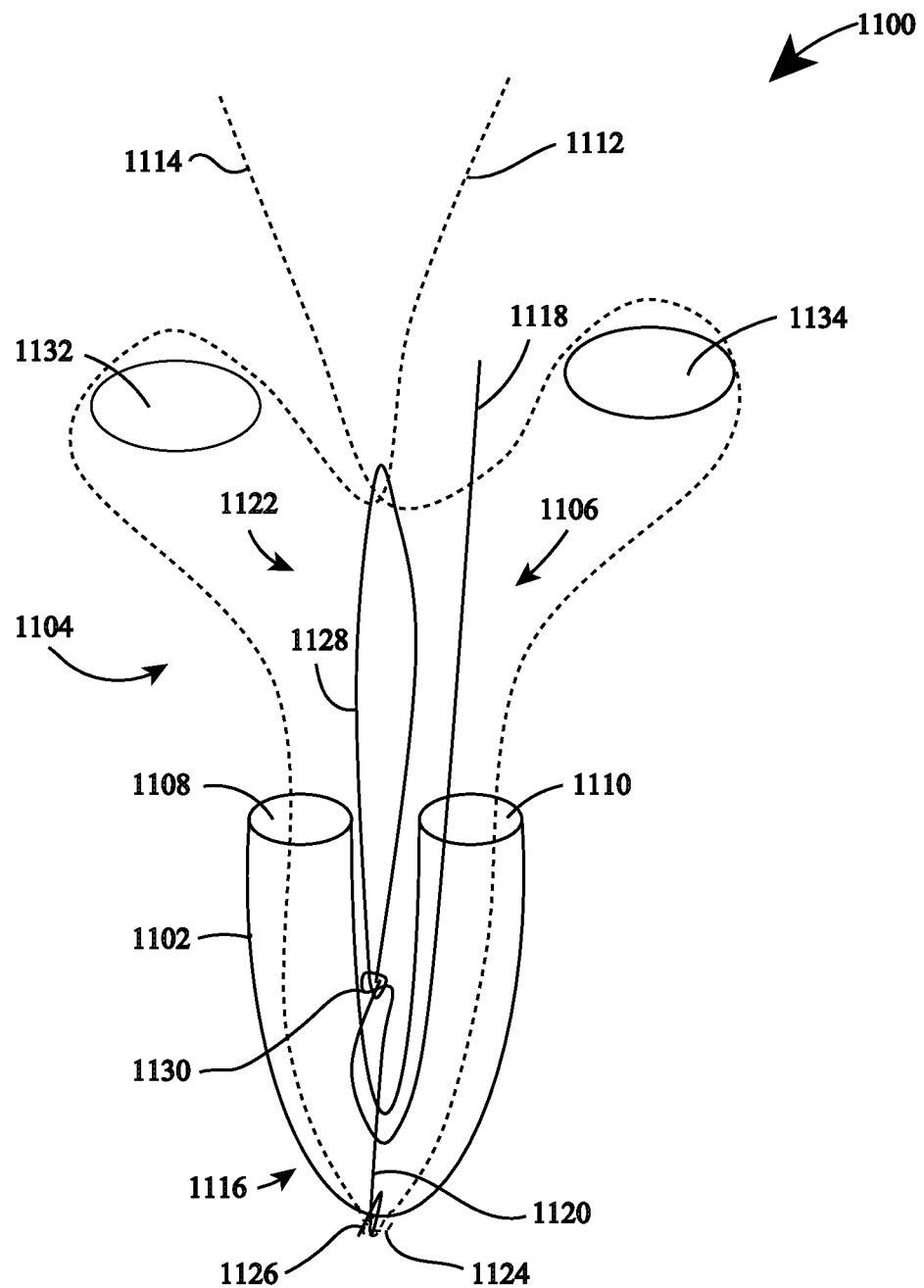
Figure 11C:
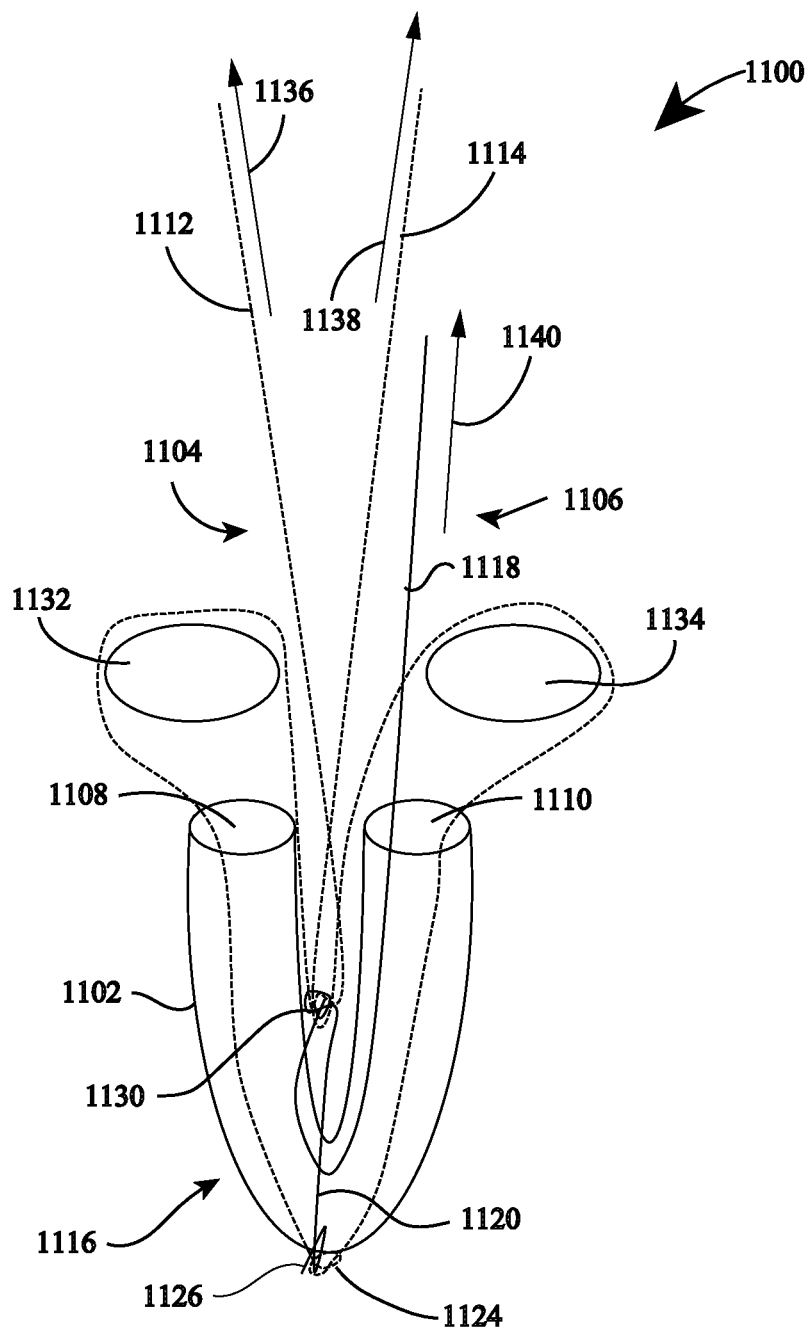

FIGS. 11A, 11B, and 11C, show a suture anchor construct 1100 in accordance with at least one example of the present disclosure. Suture anchor construct 1100 can include an anchor 1102, a first suture 1104, and a second suture 1106.

Anchor 1102 can be a soft anchor and thus deformable. A non-limiting example of a soft anchor can include a JuggerKnot anchor manufactured by Zimmer Biomet of Warsaw, Ind. Anchor 1102 can be constructed of a braided material, such as for example, a braided suture material. Anchor 1102 can have a tube shape that has a first opening 1108 and a second opening 1110. First suture 1104 and/or second suture 1106 can pass through first opening 1108 and second opening 1110. The braided material also can allow first suture 1104 and second suture 1106 to pass through anchor 1102.

First suture 1104 can have a first end 1112 (first repair end), a second end 1114 (second repair end), and an intermediate portion 1116 located in between first end 1112 and second end 1114. Second suture 1106 can have a first end 1118 (a locking strand), a second end (a fixation point) 1120, and an intermediate portion 1122 located in between first end 1118 and second end 1120.

First suture 1104 and/or second suture 1106 can be secured to anchor 1102. For example, and as shown in FIGS. 11A-11C, first suture 1104 can include a knot 1124. Knot 1124 can be tied to anchor 1102. For instance, first sutured 1104 can pass through anchor 1102 and knot 1124 can be tied. After knot 1124 is tied, first end 1112 and second end 1114 can be passed out of anchor 1102 via first opening 1108 and second opening 1110, respectively. Knot 1124 can cause first suture 1104 to be a fixed suture. Thus, upon implanting anchor 1102 into bone, tension on first end 1112 and second end 1114 can cause anchor 1102 to deform thereby seating anchor 1102 into the bone.

Second end 1120 of second suture 1106 can be secured to anchor 1102. For example, second end 1120 can pass through knot 1124 to secure second end 1120 to anchor 1102. Second end 1120 can also be tied into a separate knot 1126 to secure second end 1120 to anchor 1102. While FIGS. 11A-11C show knot 1126 tied adjacent to knot 1124, knots 1124 and 1126 need not be located adjacent to one another.

Intermediate portion 1122 can form a locking loop 1128 and a locking knot 1130. As shown in FIGS. 11A-11C, second end 1118 of second suture 1106 can pass through anchor 1102 and to form locking loop 1128 and locking knot 1130. Second end 1118 can then pass through anchor 1102 and exit anchor 1102 through second opening 1110 as shown or through first opening 1108.

As shown in FIGS. 11B and 11C, first end 1112 of first suture 1104 can be wrapped around a first tissue 1132. Second end 1114 of first suture 1104 can be wrapped around a second tissue 1134. First end 1112 and second end 1114 can then be passed through locking loop 1128.

After passing first end 1112 and second end 1114 through locking loop 1128, first end 1112 and second end 1114 can be tensioned as indicated by arrows 1136 and 1138. Tensioning of first end 1112 and second end 1114 can pull first tissue 1132 and second tissue 1134 towards anchor 1102 and seat anchor 1102 into the bone as disclosed herein.

Once first end 1112 and second end 1114 are tensioned, second end 1118 can be tensioned as indicated by arrow 1140. Tensioning of second end 1118 can cause locking loop 1128 to constrict towards locking knot 1130 thereby securing first tissue 1132 and 1134 into place. The tension within second suture 1106 can cause locking knot 1130 to tighten. The tightening of locking knot 1130 can cause locking knot 1130 to constrict movement of second suture 1106 thereby preventing locking loop 1128 from releasing tension on first end 1112 and second end 1114 of first suture 1104. First end 1112, second end 1114, and second end 1118 also can be tied together or to other sutures (not show) and/or cut off as needed.

First suture 1104 and/or second suture 1106 can include knots similar to knots 102 and 104 shown in FIGS. 4A, 4B, and 4C. For example, first end 1112 and/or second end 1114 of first suture 1104 can include a plurality of knots therealong. Each of the plurality of knots can be spaced from others. Such spacing can be a predefined distance according to some examples. The plurality of knots can facilitate coupling to first tissue 1132 and/or second tissue 1134 such as by creating a ratcheting action over and/or through first tissue 1132 and/or second tissue 1134 as described and shown with respect to tissue 68 shown in FIGS. 4A, 4B, and 4C. Furthermore, the plurality of knots can facilitate coupling with the locking loop 1128 by creating a ratcheting action that keeps first end 1112 and/or second end 1114 from easily being slackened and passed back through the locking loop 1128.

Figure 12A:
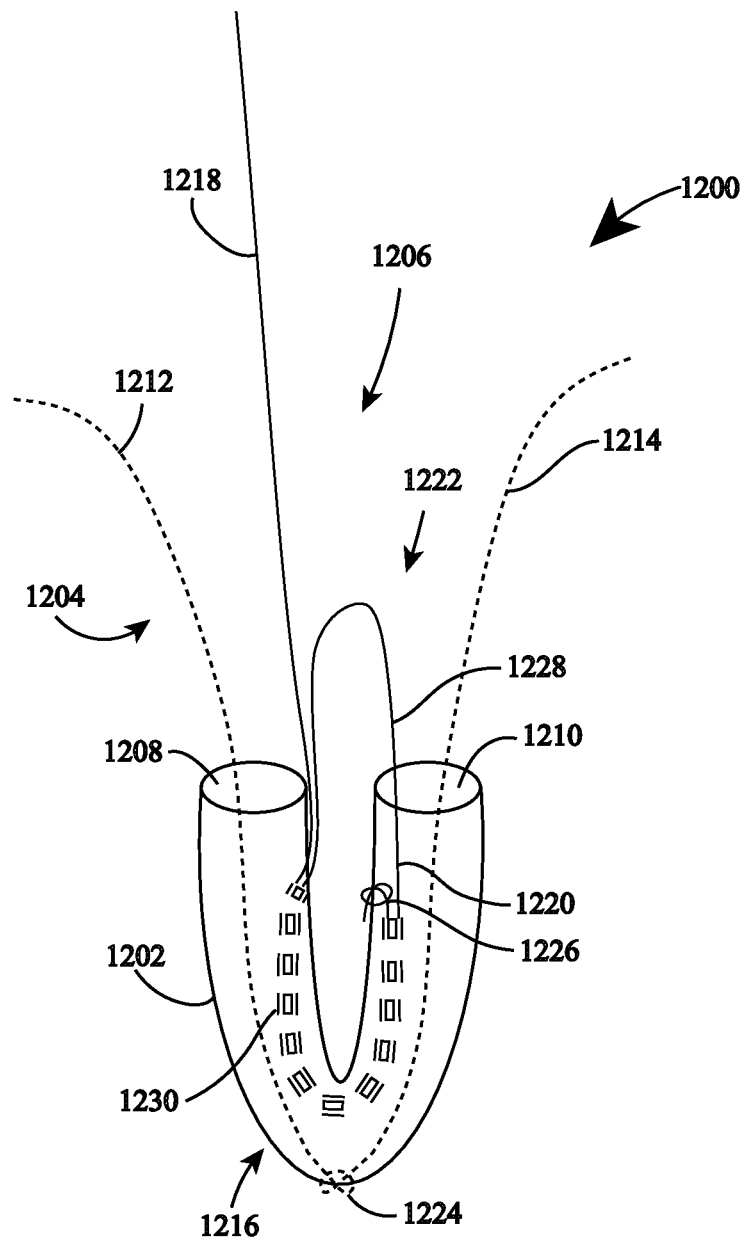
FIGS. 12A, 12B, and 12C show a suture anchor construct in accordance with at least one example of the present disclosure.
Figure 12B:
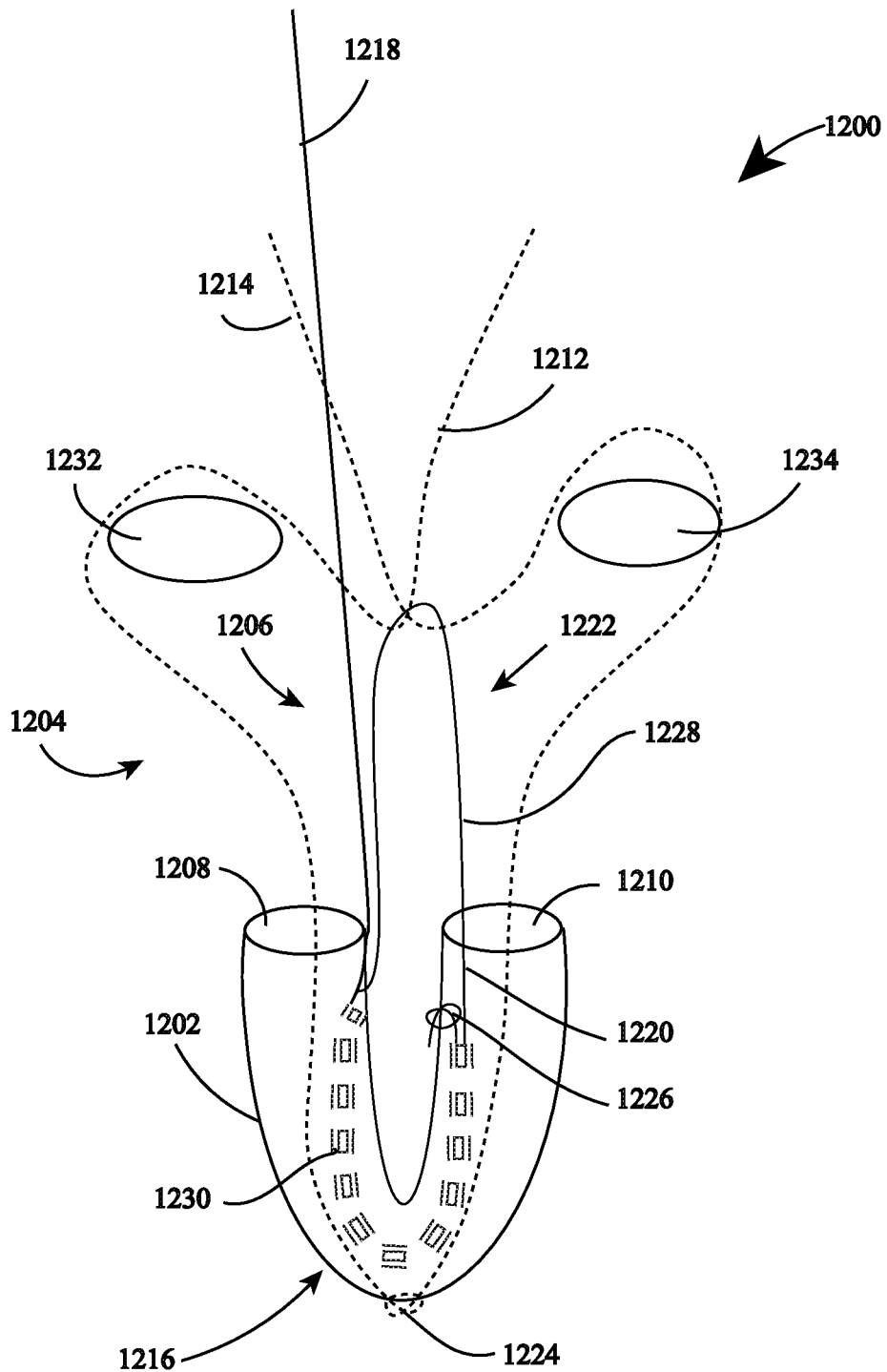
Figure 12C:
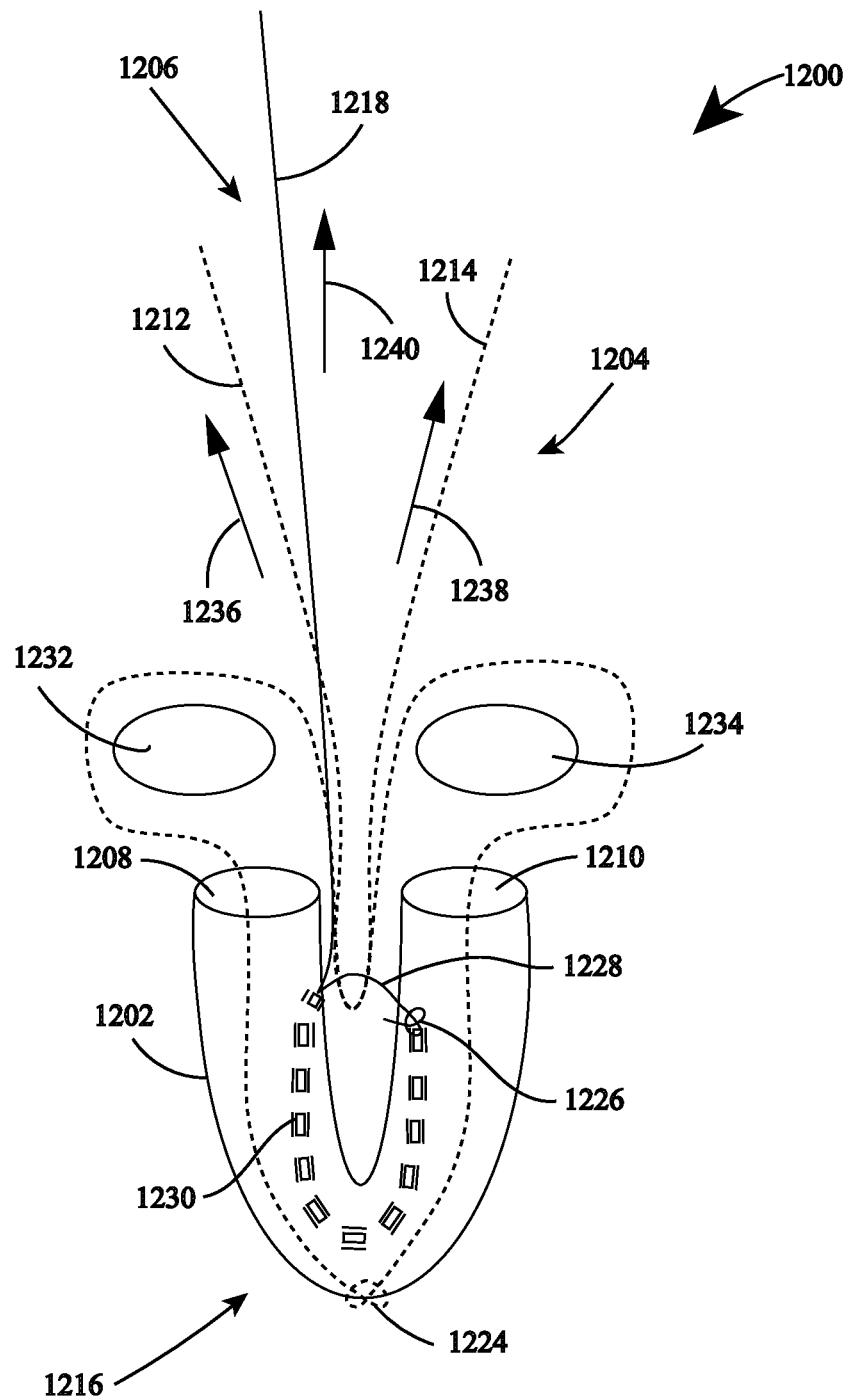

FIGS. 12A, 12B, and 12C, show a suture anchor construct 1200 in accordance with at least one example of the present disclosure. Suture anchor construct 1200 can include an anchor 1202, a first suture 1204, and a second suture 1206. Anchor 1202 can be a soft anchor and thus deformable and/or a braided material as described above with respect to anchor 1102. Anchor 1202 can have a tube shape that has a first opening 1208 and a second opening 1210. First suture 1204 and/or second suture 1206 can pass through first opening 1208 and second opening 1210. The braided material also can allow first suture 1204 and second suture 1206 to pass through anchor 1202.

First suture 1204 can have a first end 1212 (first repair end), a second end 1214 (second repair end), and an intermediate portion 1216 located in between first end 1212 and second end 1214. Second suture 1206 can have a first end 1218 (a locking strand), a second end (a fixation point) 1220, and an intermediate portion 1222 located in between first end 1218 and second end 1220.

First suture 1204 and/or second suture 1206 can be secured to anchor 1202. For example, and as shown in FIGS. 12A-12C, first suture 1204 can include a knot 1224. Knot 1224 can be tied to anchor 1202. For instance, first sutured 1204 can pass through anchor 1202 and knot 1224 can be tied. After knot 1224 is tied, first end 1212 and second end 1214 can be passed out of anchor 1202 via first opening 1208 and second opening 1210, respectively. Knot 1224 can cause first suture 1204 to be a fixed suture. Thus, upon implanting anchor 1202 into bone, tension on first end 1212 and second end 1214 can cause anchor 1202 to deform thereby seating anchor 1202 into the bone.

Second end 1220 of second suture 1206 can be secured to anchor 1202. For example, second end 1220 can pass through knot 1224 to secure second end 1220 to anchor 1202. Second end 1220 can also be tied into a separate knot 1226 to secure second end 1220 to anchor 1202. While FIGS. 12A-12C show knot 1226 tied in a different location with respect to knot 1224, knots 1224 and 1226 can be located adjacent to one another.

Intermediate portion 1222 can form a locking loop 1228. As shown in FIGS. 12A-12C, second end 1218 of second suture 1206 can pass through anchor 1202 and to form locking loop 1228. Second end 1218 can then pass through a constriction construct 1230 and anchor 1202. Constriction construct 1230 can grip and constrict movement of second suture 1206 as disclosed above with respect to constriction construct 62.

As shown in FIGS. 12B and 12C, first end 1212 of first suture 1204 can be wrapped around a first tissue 1232. Second end 1214 of first suture 1204 can be wrapped around a second tissue 1234. First end 1212 and second end 1214 can then be passed through locking loop 1228.

After passing first end 1212 and second end 1214 through locking loop 1228, first end 1212 and second end 1214 can be tensioned as indicated by arrows 1236 and 1238. Tensioning of first end 1212 and second end 1214 can pull first tissue 1232 and second tissue 1234 towards anchor 1202 and seat anchor 1202 into the bone as disclosed herein.

Once first end 1212 and second end 1214 are tensioned, second end 1218 can be tensioned as indicated by arrow 1240. Tensioning of second end 1218 can cause locking loop 1228 to constrict towards constriction construct 1230 thereby securing first tissue 1232 and 1234 into place. The tension within second suture 1206 can cause tension within constriction construct 1230 to tighten around second suture 1206. The tightening of constrictions construct 1230 can cause constriction construct 1230 to constrict movement of second suture 1206 thereby preventing locking loop 1228 from releasing tension on first end 1212 and second end 1214 of first suture 1204. First end 1212, second end 1214, and second end 1218 also can be tied together or to other sutures (not show) and/or cut off as needed.

First suture 1204 and/or second suture 1206 can include knots similar to knots 102 and 104 shown in FIGS. 4A, 4B, and 4C. For example, first end 1212 and/or second end 1214 of first suture 1204 can include a plurality of knots therealong. Each of the plurality of knots can be spaced from others. Such spacing can be a predefined distance according to some examples. The plurality of knots can facilitate coupling to first tissue 1232 and/or second tissue 1234 such as by creating a ratcheting action over and/or through first tissue 1232 and/or second tissue 1234 as described and shown with respect to tissue 68 shown in FIGS. 4A, 4B, and 4C. Furthermore, the plurality of knots can facilitate coupling with the locking loop 1228 by creating a ratcheting action that keeps first end 1212 and/or second end 1214 from easily being slackened and passed back through the locking loop 1228.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

What is claimed is:

1. A suture anchor constnict, comprising:
   a bone anchor including a suture anchoring member, the bone anchor defining: a cavity; a longitudinal passage extending from a trailing end of the bone anchor at least partially through the bone anchor to the cavity; and a first radial passage extending through the bone anchor and intersecting the longitudinal passage proximate the trailing end of the bone anchor; wherein the first radial passage extends from a first side opening in an exterior surface of the bone anchor to a second side opening in the exterior surface of the bone anchor, and wherein the suture anchoring member is located in the cavity;
   a suture coupled to the suture anchoring member and including a tensioning portion, a repair portion, and an intermediate portion, the intermediate portion forming a suture loop extending along the longitudinal passage; and
   a snare extending: into the hone anchor through the first side opening in the exterior surface of the bone anchor; along the first radial passage so as to pass through the suture loop extending along the longitudinal passage; and out of the bone anchor through the second side opening in the exterior surface of the bone anchor, wherein the snare defines a snare loop sized to allow a portion of the repair portion to pass through the snare loop.

2. The suture anchor construct of claim 1, wherein the tension portion extends from the suture anchoring member through the longitudinal passage.

3. The suture anchor construct of claim 1, wherein the repair portion of the suture includes one or more protuberances.

4. The suture anchor construct of claim 1, wherein a portion of the repair portion passes through the suture loop.

5. The suture anchor construct of claim 1, wherein the repair portion extends from the suture anchoring member through the longitudinal passage.

6. The suture anchor construct of claim 1, wherein the intermediate portion comprises a constriction construct.

7. The suture anchor construct of claim I, wherein the repair portion includes a knot configured to prevent the repair portion from being drawn further around the suture anchoring member during or after tensioning of at least one of the tensioning portion and the repair portion.

8. The suture anchor construct of claim 1 further comprising:
   a second radial passage extending through the bone anchor, the second radial passage located between the first radial passage and a leading end of the bone anchor, the suture anchoring member located proximate the second radial passage.

9. The suture anchor construct of claim 8, wherein a portion of the repair portion passes through the second radial passage.

10. The suture anchor construct of claim 8, wherein an end of the repair portion exits the bone anchor through the second radial passage and extends back along the exterior surface of the bone anchor toward the trailing end of the bone anchor.

11. The suture anchor construct of claim 10, wherein the end of the repair portion is positioned outside the bone anchor proximate the trailing end of the bone anchor so as to make the end of the repair portion available for grasping by the snare for pulling the end of the repair portion:
   into the bone anchor through the second side opening in the exterior surface of the bone anchor;
   along the first radial passage; through the suture loop extending along the longitudinal passage; and
   out of the bone anchor through the first side opening in the exterior surface of the bone anchor.

12. The suture anchor construct of claim 1, wherein a portion of the repair portion passes through the first radial passage.

13. The suture anchor construct of claim 1, wherein the trailing end of the bone anchor includes a trailing end opening from which the longitudinal passage extends toward a leading end of the bone anchor.

14. The suture anchor construct of claim 13, wherein the snare extends into the bone anchor and along the first radial passage without passing through the trailing end opening.

15. A suture anchor construct, comprising:
   a bone anchor including a suture anchoring member, the bone anchor defining:
   a first radial passage located proximate a trailing end of the bone anchor; wherein the first radial passage extends through the bone anchor from a first side opening in an exterior surface of the bone anchor to a second side opening in the exterior surface of the bone anchor;
   a second radial passage located in between the first radial passage and a leading end of the bone anchor, the suture anchoring member located in the second radial passage, wherein the second radial passage extends through the bone anchor from a third side opening in the exterior surface of the bone anchor to a fourth side opening in the exterior surface of the bone anchor; and
   a longitudinal passage extending from the trailing end of the bone anchor to the second radial passage, the longitudinal passage intersecting the first radial passage;
   a suture including a tensioning portion, a repair portion, and an intermediate portion located in between the tensioning portion and the repair portion, the repair portion extending from the suture anchoring member, the intermediate portion forming a suture loop extending along the longitudinal passage; and
   a snare extending: into the bone anchor through the first side opening in the exterior surface of the bone anchor; along the first radial passage so as to pass through the suture loop extending along the longitudinal passage; and out of the bone anchor through the second side opening in the exterior surface of the bone anchor.

16. The suture anchor construct of claim 15, wherein the snare defines a snare loop sized to allow a second end of the repair portion to pass through the snare loop.

17. The suture anchor construct of claim 15, wherein the repair portion of the suture includes one or more knots.

18. The suture anchor construct of claim 15, wherein a portion of the repair portion is wrapped around the suture anchoring member.

19. The suture anchor construct of claim 15, wherein a portion of the repair portion passes through the suture loop.

* * * * *

UNITED STATES PATENT AND TRADEMARK OFFICE
CERTIFICATE OF CORRECTION

PATENT NO. : 11,826,038 B2
APPLICATION NO. : 17/076401
DATED : November 28, 2023
INVENTOR(S) : Winslow et al.

Page 1 of 1

It is certified that error appears in the above-identified patent and that said Letters Patent is hereby corrected as shown below:

In the Claims

In Column 18, Line 34, in Claim 1, delete "constnict," and insert --construct,-- therefor In Column 18, Line 41, in Claim 1, delete "anchor;" and insert --anchor,-- therefor In Column 18, Line 51, in Claim 1, delete "hone" and insert --bone-- therefor In Column 19, Line 6, in Claim 7, delete "claim I," and insert --claim 1,-- therefor In Column 20, Line 5, in Claim 15, delete "anchor;" and insert --anchor,-- therefor Signed and Sealed this
Twenty-third Day of April, 2024

Katherine Kelly Vidal
*Director of the United States Patent and Trademark Office*